(12) United States Patent
Graham et al.

(10) Patent No.: US 7,892,725 B2
(45) Date of Patent: *Feb. 22, 2011

(54) PROCESS FOR STORING A SPERM DISPERSION

(75) Inventors: Jeffrey A. Graham, Chesterfield, MO (US); Cindy L. Ludwig, St. Louis, MO (US); Kathleen S. Crowley, Webster Groves, MO (US)

(73) Assignee: Inguran, LLC, Navasota, TX (US)

( * ) Notice: Subject to any disclaimer, the term of this patent is extended or adjusted under 35 U.S.C. 154(b) by 233 days.

This patent is subject to a terminal disclaimer.

(21) Appl. No.: 11/092,338

(22) Filed: Mar. 29, 2005

(65) Prior Publication Data

US 2005/0214733 A1    Sep. 29, 2005

Related U.S. Application Data

(60) Provisional application No. 60/618,440, filed on Oct. 13, 2004, provisional application No. 60/614,178, filed on Sep. 29, 2004, provisional application No. 60/557,407, filed on Mar. 29, 2004.

(51) Int. Cl.
*A01N 1/02* (2006.01)

(52) U.S. Cl. .............................. 435/2; 422/73; 435/325; 435/6

(58) Field of Classification Search ........................ 435/2
See application file for complete search history.

(56) References Cited

U.S. PATENT DOCUMENTS

| | | | |
|---|---|---|---|
| 3,005,756 A | 10/1961 | Van Demark et al. |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister et al. |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| RE29,141 E | 2/1977 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |

(Continued)

FOREIGN PATENT DOCUMENTS

BR          9704313          6/1999

(Continued)

OTHER PUBLICATIONS

Garner et al., Effect of Semen dilution on bovine sperm viability as determined by dual-DNA staining and Flow cytometry, Journal of Andrology, vol. 18, No. 3, 1997, p. 324-331.*

(Continued)

*Primary Examiner*—Ralph Gitomer
*Assistant Examiner*—Tiffany M Gough
(74) *Attorney, Agent, or Firm*—Cindee Ewell; Ryan S. Christensen; Inguran, LLC

(57) ABSTRACT

Processes of storing sorted and unsorted spermatozoa, in the form of a sperm dispersion, having reduced motility relative to endogenous ejaculated sperm are disclosed. The immotile spermatozoa of the dispersion tend to have a greater capacity for enduring the rigors associated with storage, transportation, and fertilization procedures. Processes for providing such sperm dispersions, for inseminating a female mammal with such sperm dispersions, as well as compositions and combinations comprising the sperm dispersions, are also disclosed.

20 Claims, No Drawings

U.S. PATENT DOCUMENTS

| | | |
|---|---|---|
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,251,733 A | 2/1981 | Hirleman, Jr. |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou et al. |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junnila |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | de Grooth et al. |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |

| | | | | | |
|---|---|---|---|---|---|
| 5,162,306 A | 11/1992 | Donaldson | 5,620,842 A | 4/1997 | Davis et al. |
| 5,167,926 A | 12/1992 | Kimura et al. | 5,622,820 A | 4/1997 | Rossi |
| 5,180,065 A | 1/1993 | Touge et al. | 5,627,037 A | 5/1997 | Ward et al. |
| 5,182,617 A | 1/1993 | Yoneyama et al. | 5,633,503 A | 5/1997 | Kosaka |
| 5,195,979 A | 3/1993 | Schinkel et al. | 5,641,457 A | 6/1997 | Vardanega et al. |
| 5,199,576 A | 4/1993 | Corio et al. | 5,643,796 A | 7/1997 | Van den Engh et al. |
| 5,204,884 A | 4/1993 | Leary et al. | 5,650,847 A | 7/1997 | Maltsev et al. |
| 5,215,376 A | 6/1993 | Schulte et al. | 5,658,751 A | 8/1997 | Yue et al. |
| 5,219,729 A | 6/1993 | Hodgen | 5,660,997 A | 8/1997 | Spaulding |
| 5,247,339 A | 9/1993 | Ogino | 5,663,048 A | 9/1997 | Winkfein et al. |
| 5,259,593 A | 11/1993 | Orme et al. | 5,665,315 A | 9/1997 | Robert et al. |
| 5,260,764 A | 11/1993 | Fukuda et al. | 5,672,880 A | 9/1997 | Kain |
| 5,274,240 A | 12/1993 | Mathies et al. | 5,674,743 A | 10/1997 | Ulmer |
| 5,275,787 A | 1/1994 | Yuguchi et al. | 5,675,401 A | 10/1997 | Wangler et al. |
| 5,298,967 A | 3/1994 | Wells | 5,682,038 A | 10/1997 | Hoffman |
| 5,315,122 A | 5/1994 | Pinsky et al. | 5,684,575 A | 11/1997 | Steen |
| 5,316,540 A | 5/1994 | McMannis et al. | 5,687,727 A | 11/1997 | Kraus et al. |
| 5,317,162 A | 5/1994 | Pinsky et al. | 5,690,815 A | 11/1997 | Krasnoff et al. |
| 5,346,990 A | 9/1994 | Spaulding | 5,690,895 A | 11/1997 | Matsumoto et al. |
| RE34,782 E | 11/1994 | Dandliker et al. | 5,691,133 A | 11/1997 | Critser et al. |
| 5,359,907 A | 11/1994 | Baker et al. | 5,693,534 A | 12/1997 | Alak et al. |
| 5,366,888 A | 11/1994 | Fry et al. | 5,696,157 A | 12/1997 | Wang et al. |
| 5,367,474 A | 11/1994 | Auer et al. | 5,700,692 A | 12/1997 | Sweet |
| 5,370,842 A | 12/1994 | Miyazaki et al. | 5,701,012 A | 12/1997 | Ho |
| 5,371,585 A | 12/1994 | Morgan et al. | 5,707,808 A | 1/1998 | Roslaniec et al. |
| 5,395,588 A | 3/1995 | North, Jr. et al. | 5,708,868 A | 1/1998 | Ishikawa |
| 5,400,179 A | 3/1995 | Ito | 5,712,807 A | 1/1998 | Bangham |
| 5,412,466 A | 5/1995 | Ogino | 5,719,666 A | 2/1998 | Fukuda et al. |
| 5,437,987 A | 8/1995 | Teng et al. | 5,719,667 A | 2/1998 | Miers |
| 5,439,362 A | 8/1995 | Spaulding | 5,726,009 A | 3/1998 | Connors et al. |
| 5,444,527 A | 8/1995 | Kosaka | 5,726,364 A | 3/1998 | Van den Engh |
| 5,447,841 A | 9/1995 | Gray et al. | 5,726,751 A | 3/1998 | Altendorf et al. |
| 5,447,842 A | 9/1995 | Simons | 5,730,941 A | 3/1998 | Lefevre et al. |
| 5,452,054 A | 9/1995 | Dewa et al. | 5,736,330 A | 4/1998 | Fulton |
| 5,457,526 A | 10/1995 | Kosaka | 5,739,902 A | 4/1998 | Gjelsnes et al. |
| 5,461,145 A | 10/1995 | Kudo et al. | 5,745,308 A | 4/1998 | Spangenberg |
| 5,464,581 A | 11/1995 | van den Engh | 5,747,349 A | 5/1998 | van den Engh et al. |
| 5,466,572 A | 11/1995 | Sasaki et al. | 5,777,732 A | 7/1998 | Hanninen et al. |
| 5,467,189 A | 11/1995 | Kreikebaum et al. | 5,780,230 A | 7/1998 | Li et al. |
| 5,469,375 A | 11/1995 | Kosaka | 5,786,560 A | 7/1998 | Tatah et al. |
| 5,471,294 A | 11/1995 | Ogino | 5,790,692 A | 8/1998 | Price et al. |
| 5,471,299 A | 11/1995 | Kaye et al. | 5,793,485 A | 8/1998 | Gourley |
| 5,475,487 A | 12/1995 | Mariella, Jr. et al. | 5,795,767 A | 8/1998 | Tsukada et al. |
| 5,480,774 A | 1/1996 | Hew et al. | 5,796,112 A | 8/1998 | Ichie |
| 5,480,775 A | 1/1996 | Ito et al. | 5,798,276 A | 8/1998 | Haugland et al. |
| 5,483,469 A | 1/1996 | Van den Engh et al. | 5,799,830 A | 9/1998 | Carroll et al. |
| 5,488,469 A | 1/1996 | Yamamoto et al. | 5,804,436 A | 9/1998 | Okun et al. |
| 5,492,534 A | 2/1996 | Athayde et al. | 5,815,262 A | 9/1998 | Schrof et al. |
| 5,494,795 A | 2/1996 | Guerry et al. | 5,819,948 A | 10/1998 | Van den Engh |
| 5,495,719 A | 3/1996 | Gray, Jr. | 5,824,269 A | 10/1998 | Kosaka et al. |
| 5,496,272 A | 3/1996 | Chung et al. | 5,831,723 A | 11/1998 | Kubota et al. |
| 5,503,994 A | 4/1996 | Shear et al. | 5,835,262 A | 11/1998 | Iketaki et al. |
| 5,514,537 A | 5/1996 | Chandler | 5,840,504 A | 11/1998 | Blecher |
| 5,523,573 A | 6/1996 | Hanninen et al. | 5,844,685 A | 12/1998 | Gontin |
| 5,532,155 A | 7/1996 | Ranoux | 5,846,737 A | 12/1998 | Kang |
| 5,547,849 A | 8/1996 | Baer et al. | 5,866,344 A | 2/1999 | Georgiou |
| 5,548,395 A | 8/1996 | Kosaka | 5,868,767 A | 2/1999 | Farley et al. |
| 5,548,661 A | 8/1996 | Price et al. | 5,872,627 A | 2/1999 | Miers |
| 5,550,058 A | 8/1996 | Corio et al. | 5,873,254 A | 2/1999 | Arav |
| 5,556,764 A | 9/1996 | Sizto et al. | 5,874,266 A | 2/1999 | Palsson |
| 5,558,998 A | 9/1996 | Hammond et al. | 5,876,942 A | 3/1999 | Cheng et al. |
| 5,559,032 A | 9/1996 | Pomeroy et al. | 5,880,457 A | 3/1999 | Tomiyama et al. |
| 5,578,449 A | 11/1996 | Fr asch et al. | 5,880,474 A | 3/1999 | Norton et al. |
| 5,579,159 A | 11/1996 | Ito | 5,883,378 A | 3/1999 | Irish et al. |
| 5,584,982 A | 12/1996 | Dovichi et al. | 5,888,730 A | 3/1999 | Gray et al. |
| 5,589,457 A | 12/1996 | Wiltbank et al. | 5,891,734 A | 4/1999 | Gill et al. |
| 5,596,401 A | 1/1997 | Kusuzawa | 5,893,843 A | 4/1999 | Rodrigues Claro |
| 5,601,234 A | 2/1997 | Larue | 5,895,764 A | 4/1999 | Sklar et al. |
| 5,601,235 A | 2/1997 | Booker et al. | 5,895,922 A | 4/1999 | Ho |
| 5,601,533 A | 2/1997 | Hancke et al. | 5,899,848 A | 5/1999 | Haubrich |
| 5,602,039 A | 2/1997 | Van den Engh | 5,909,278 A | 6/1999 | Deka et al. |
| 5,602,349 A | 2/1997 | Van den Engh | 5,912,257 A | 6/1999 | Prasad et al. |
| 5,608,519 A | 3/1997 | Gourley et al. | 5,916,144 A | 6/1999 | Li et al. |

| | | | | | | |
|---|---|---|---|---|---|---|
| 5,916,449 | A | 6/1999 | Ellwart et al. | 6,465,169 B2 | 10/2002 | Walderich et al. |
| 5,917,733 | A | 6/1999 | Bangham | 6,473,176 B2 | 10/2002 | Basiji et al. |
| 5,919,360 | A | 7/1999 | Contaxis, III et al. | 6,482,652 B2 | 11/2002 | Furlong et al. |
| 5,919,621 | A | 7/1999 | Brown | 6,489,092 B1 | 12/2002 | Benjamin et al. |
| 5,934,885 | A | 8/1999 | Farrell et al. | 6,495,333 B1 | 12/2002 | Willmann et al. |
| 5,962,238 | A | 10/1999 | Sizto et al. | 6,495,366 B1 | 12/2002 | Briggs |
| 5,972,710 | A | 10/1999 | Weigl et al. | 6,503,698 B1 | 1/2003 | Dobrinsky et al. |
| 5,973,842 | A | 10/1999 | Spangenberg | 6,511,853 B1 | 1/2003 | Kopf-Sill et al. |
| 5,985,538 | A | 11/1999 | Stachecki | 6,514,722 B2 | 2/2003 | Palsson et al. |
| 5,991,028 | A | 11/1999 | Cabib et al. | 6,524,860 B1 | 2/2003 | Seidel et al. |
| 5,998,212 | A | 12/1999 | Corio et al. | 6,528,802 B1 | 3/2003 | Koenig et al. |
| 6,002,471 | A | 12/1999 | Quake | 6,534,308 B1 | 3/2003 | Palsson et al. |
| 6,003,678 | A | 12/1999 | Van den Engh | 6,537,829 B1 | 3/2003 | Zarling et al. |
| 6,039,815 | A | 3/2000 | Yeol et al. | 6,540,895 B1 | 4/2003 | Spence et al. |
| 6,042,249 | A | 3/2000 | Spangenberg | 6,563,583 B2 | 5/2003 | Ortyn et al. |
| 6,050,935 | A | 4/2000 | Ranoux et al. | 6,576,291 B2 | 6/2003 | Bawendi et al. |
| 6,071,689 | A | 6/2000 | Seidel et al. | 6,577,387 B2 | 6/2003 | Ross, III et al. |
| 6,079,836 | A | 6/2000 | Burr et al. | 6,580,504 B1 | 6/2003 | Ortyn et al. |
| 6,086,574 | A | 7/2000 | Carroll et al. | 6,587,203 B2 | 7/2003 | Colon |
| 6,087,352 | A | 7/2000 | Trout | 6,589,792 B1 | 7/2003 | Malachowski |
| 6,097,485 | A | 8/2000 | Lievan | 6,590,911 B1 | 7/2003 | Spinelli et al. |
| 6,111,398 | A | 8/2000 | Graham | 6,596,143 B1 | 7/2003 | Wang et al. |
| 6,117,068 | A | 9/2000 | Gourley et al. | 6,596,499 B2 | 7/2003 | Jalink |
| 6,119,465 | A | 9/2000 | Mullens et al. | 6,604,435 B2 | 8/2003 | Buchanan et al. |
| 6,120,735 | A | 9/2000 | Zborowski et al. | 6,613,525 B2 | 9/2003 | Nelson et al. |
| 6,128,133 | A | 10/2000 | Bergmann | 6,617,107 B1 | 9/2003 | Dean |
| 6,130,034 | A | 10/2000 | Aitken | 6,618,143 B2 | 9/2003 | Roche et al. |
| 6,132,961 | A | 10/2000 | Gray et al. | 6,618,679 B2 | 9/2003 | Loehrlein et al. |
| 6,133,044 | A | 10/2000 | Van den Engh | 6,641,708 B1 | 11/2003 | Huang et al. |
| 6,133,995 | A | 10/2000 | Kubota | 6,642,018 B1 | 11/2003 | Koller et al. |
| 6,139,800 | A | 10/2000 | Chandler | 6,658,357 B2 | 12/2003 | Chandler |
| 6,140,121 | A | 10/2000 | Ellington et al. | 6,664,550 B2 | 12/2003 | Rader et al. |
| 6,143,535 | A | 11/2000 | Palsson | 6,667,830 B1 | 12/2003 | Iketaki et al. |
| 6,146,837 | A | 11/2000 | van de Winkel | 6,671,044 B2 | 12/2003 | Ortyn et al. |
| 6,153,373 | A | 11/2000 | Benjamin et al. | 6,673,095 B2 | 1/2004 | Nordquist |
| 6,154,276 | A | 11/2000 | Mariella, Jr. | 6,674,525 B2 | 1/2004 | Bardell et al. |
| 6,175,409 | B1 | 1/2001 | Nielsen et al. | 6,698,627 B2 | 3/2004 | Garcia et al. |
| 6,177,277 | B1 | 1/2001 | Soini | 6,700,130 B2 | 3/2004 | Fritz |
| 6,193,647 | B1 | 2/2001 | Beebe et al. | 6,703,621 B2 | 3/2004 | Wolleschensky |
| 6,201,628 | B1 | 3/2001 | Basiji et al. | 6,704,313 B1 | 3/2004 | Duret et al. |
| 6,208,411 | B1 | 3/2001 | Vaez-Iravani | 6,706,163 B2 | 3/2004 | Seul et al. |
| 6,211,477 | B1 | 4/2001 | Cardott et al. | 6,707,555 B1 | 3/2004 | Kusuzawa et al. |
| 6,214,560 | B1 | 4/2001 | Yguerabide et al. | 6,713,019 B2 | 3/2004 | Ozasa et al. |
| 6,221,654 | B1 | 4/2001 | Quake et al. | 6,729,369 B2 | 5/2004 | Neas et al. |
| 6,221,671 | B1 | 4/2001 | Groner et al. | 6,746,873 B1 | 6/2004 | Buchanan et al. |
| 6,238,920 | B1 | 5/2001 | Nagai et al. | 6,752,298 B2 | 6/2004 | Garcia et al. |
| 6,248,590 | B1 | 6/2001 | Malachowski | 6,753,161 B2 | 6/2004 | Koller et al. |
| 6,256,096 | B1 | 7/2001 | Johnson | 6,761,286 B2 | 7/2004 | Py et al. |
| 6,283,920 | B1 | 9/2001 | Eberle et al. | 6,761,288 B2 | 7/2004 | Garcia |
| 6,296,810 | B1 | 10/2001 | Ulmer | 6,767,706 B2 | 7/2004 | Quake et al. |
| 6,309,815 | B1 | 10/2001 | Tash et al. | 6,780,377 B2 | 8/2004 | Hall et al. |
| 6,316,234 | B1 | 11/2001 | Bova | 6,782,768 B2 | 8/2004 | Buchanan et al. |
| 6,317,511 | B1 | 11/2001 | Horiuchi | 6,789,706 B2 | 9/2004 | Abergel et al. |
| 6,323,632 | B1 | 11/2001 | Husher et al. | 6,789,759 B2 | 9/2004 | Miyasaka et al. |
| 6,328,071 | B1 | 12/2001 | Austin | 6,793,387 B1 | 9/2004 | Neas et al. |
| 6,329,158 | B1 | 12/2001 | Hoffman et al. | 6,813,017 B1 | 11/2004 | Hoffman et al. |
| 6,332,540 | B1 | 12/2001 | Paul et al. | 6,819,411 B1 | 11/2004 | Sharpe et al. |
| 6,357,307 | B2 | 3/2002 | Buchanan et al. | 6,849,423 B2 | 2/2005 | Mutz et al. |
| 6,368,786 | B1 | 4/2002 | Saint-Ramon et al. | 6,861,265 B1 | 3/2005 | den Engh |
| 6,372,422 | B1 | 4/2002 | Seidel et al. | 6,941,005 B2 | 9/2005 | Lary et al. |
| 6,372,506 | B1 | 4/2002 | Norton | 7,015,310 B2 | 3/2006 | Remington |
| 6,384,951 | B1 | 5/2002 | Basiji et al. | 7,094,527 B2 | 8/2006 | Seidel et al. |
| 6,395,305 | B1 | 5/2002 | Buhr et al. | 7,105,355 B2 | 9/2006 | Kurabayashi et al. |
| 6,400,453 | B1 | 6/2002 | Hansen | 7,195,920 B2 | 3/2007 | Seidel et al. |
| 6,411,835 | B1 | 6/2002 | Modell et al. | 7,208,265 B1 | 4/2007 | Schenk |
| 6,411,904 | B1 | 6/2002 | Chandler | 7,221,453 B2 | 5/2007 | Sharpe et al. |
| 6,423,505 | B1 | 7/2002 | Davis | 2001/0006416 A1 | 7/2001 | Johnson |
| 6,432,630 | B1 | 8/2002 | Blankenstein | 2002/0047697 A1 | 4/2002 | Husher et al. |
| 6,432,638 | B2 | 8/2002 | Dervan et al. | 2002/0058332 A1 | 5/2002 | Quake et al. |
| 6,452,372 | B1 | 9/2002 | Husher et al. | 2002/0064809 A1 | 5/2002 | Mutz et al. |
| 6,454,945 | B1 | 9/2002 | Weigl et al. | 2002/0096123 A1 | 7/2002 | Whittier et al. |
| 6,456,055 | B2 | 9/2002 | Shinabe et al. | 2002/0115055 A1 | 8/2002 | Matta |
| 6,463,314 | B1 | 10/2002 | Haruna | 2002/0119558 A1 | 8/2002 | Seidel et al. |

| | | | | | | |
|---|---|---|---|---|---|---|
| 2002/0131957 A1 | 9/2002 | Gavin | | EP | 0 317 809 A2 | 5/1989 |
| 2002/0171827 A1 | 11/2002 | Van den Engh | | EP | A-0 366794 | 5/1990 |
| 2002/0182590 A1 | 12/2002 | Strange et al. | | EP | 0 409 293 A2 | 1/1991 |
| 2002/0186375 A1 | 12/2002 | Asbury et al. | | EP | 0 461 618 | 12/1991 |
| 2002/0186874 A1 | 12/2002 | Price et al. | | EP | 0 463 562 A1 | 1/1992 |
| 2002/0198928 A1 | 12/2002 | Bukshpan et al. | | EP | 0468100 A1 | 1/1992 |
| 2003/0048433 A1 | 3/2003 | Desjonqueres | | EP | 0474 187 A2 | 3/1992 |
| 2003/0059764 A1 | 3/2003 | Ravkin et al. | | EP | 0 316 172 B1 | 7/1992 |
| 2003/0059945 A1 | 3/2003 | Dzekunov et al. | | EP | 0 316 171 B1 | 9/1992 |
| 2003/0078703 A1 | 4/2003 | Potts | | EP | 0570102 A1 | 3/1993 |
| 2003/0096405 A1 | 5/2003 | Takayama et al. | | EP | 0538786 A | 4/1993 |
| 2003/0098421 A1 | 5/2003 | Ho | | EP | 0 279 000 B1 | 7/1993 |
| 2003/0119050 A1 | 6/2003 | Shai | | EP | 0 553 951 A1 | 8/1993 |
| 2003/0119206 A1 | 6/2003 | Shai | | EP | 0 288 029 B1 | 1/1994 |
| 2003/0129091 A1 | 7/2003 | Seidel et al. | | EP | 0 381 694 B1 | 6/1994 |
| 2003/0157475 A1 | 8/2003 | Schenk | | EP | 0 361 504 B1 | 7/1994 |
| 2003/0165812 A1 | 9/2003 | Takayama et al. | | EP | 606847 A2 | 7/1994 |
| 2003/0175917 A1 | 9/2003 | Cumming | | EP | 0 289 200 B2 | 8/1994 |
| 2003/0175980 A1 | 9/2003 | Hayenga et al. | | EP | 0 555 212 B1 | 10/1994 |
| 2003/0190681 A1 | 10/2003 | Shai | | EP | 0 361 503 B1 | 11/1994 |
| 2003/0207461 A1 | 11/2003 | Bell et al. | | EP | 0 696 731 A2 | 2/1996 |
| 2003/0209059 A1 | 11/2003 | Kawano | | EP | 0 705 978 A2 | 4/1996 |
| 2004/0005582 A1 | 1/2004 | Shipwash | | EP | 0 711 991 A1 | 5/1996 |
| 2004/0031071 A1 | 2/2004 | Morris et al. | | EP | 0 471 758 B1 | 9/1996 |
| 2004/0034879 A1 | 2/2004 | Rothstein et al. | | EP | 0 736 765 A1 | 10/1996 |
| 2004/0049801 A1 | 3/2004 | Seidel | | EP | 0 545 284 B1 | 2/1997 |
| 2004/0053243 A1 | 3/2004 | Evans | | EP | 0 360 487 B1 | 7/1997 |
| 2004/0055030 A1 | 3/2004 | Maxwell et al. | | EP | 0 412 431 B1 | 10/1997 |
| 2004/0061070 A1 | 4/2004 | Hansen | | EP | 0 526 131 B1 | 1/1998 |
| 2004/0061853 A1 | 4/2004 | Blasenheim | | EP | A-0 478155 | 1/1998 |
| 2004/0062685 A1 | 4/2004 | Norton et al. | | EP | 0 822 404 A3 | 2/1998 |
| 2004/0107150 A1 | 6/2004 | Neas et al. | | EP | 0 822 401 A2 | 4/1998 |
| 2004/0132001 A1 | 7/2004 | Seidel et al. | | EP | 0 556 748 B1 | 10/1998 |
| 2005/0003472 A1 | 1/2005 | Anzar et al. | | EP | 0 430 402 B1 | 1/1999 |
| 2005/0011582 A1 | 1/2005 | Haug | | EP | 0 529 666 B1 | 4/2000 |
| 2005/0064383 A1 | 3/2005 | Bashkin et al. | | EP | 0 994 342 A3 | 4/2000 |
| 2005/0112541 A1 | 5/2005 | Durack et al. | | EP | 0 752 133 B1 | 6/2000 |
| 2005/0214733 A1 | 9/2005 | Graham | | EP | 1 018 644 A2 | 7/2000 |
| 2005/0244805 A1 | 11/2005 | Ludwig et al. | | EP | 1033802 A2 | 1/2001 |
| 2005/0028224 A1 | 12/2005 | Ludwig et al. | | EP | 1 118 268 A1 | 7/2001 |
| 2006/0118167 A1 | 6/2006 | Neas et al. | | EP | 1 147 774 A1 | 10/2001 |
| 2006/0147894 A1 | 7/2006 | Sowter | | EP | 0 534 033 B1 | 11/2001 |
| 2006/0263829 A1 | 11/2006 | Evans et al. | | EP | 0925 494 B1 | 12/2001 |
| 2006/0281176 A1 | 12/2006 | Seidel et al. | | EP | 0 748 316 B1 | 5/2002 |
| 2007/0017086 A1 | 1/2007 | McFadyen | | EP | 0 662 124 B1 | 6/2002 |
| 2007/0026378 A1 | 2/2007 | Schenk | | EP | 1 245 944 A3 | 10/2002 |
| 2007/0026379 A1 | 2/2007 | Seidel et al. | | EP | 1 249 502 A2 | 10/2002 |
| 2007/0042342 A1 | 2/2007 | Seidel et al. | | EP | 1250897 A1 | 10/2002 |
| 2007/0092860 A1 | 4/2007 | Schenk | | EP | 1 380 304 A2 | 1/2004 |
| 2007/0099171 A1 | 5/2007 | Schenk | | EP | 1 403 633 A3 | 4/2004 |
| 2007/0099260 A1 | 5/2007 | Seidel et al. | | EP | 1 100 400 B1 | 5/2004 |
| | | | | EP | 1 257 168 B1 | 2/2005 |
| FOREIGN PATENT DOCUMENTS | | | | GB | 1471019 | 4/1977 |
| | | | | GB | 2 121 976 A | 1/1984 |
| CA | 1029833 | 4/1978 | | GB | 2 122 369 A | 1/1984 |
| CA | 1250808 | 3/1989 | | GB | 2 125 181 A | 2/1984 |
| CA | 2 113 957 A1 | 1/1994 | | GB | 2 136 561 A | 9/1984 |
| CN | 03109426 | 12/2005 | | GB | 2 137 352 A | 10/1984 |
| EP | 0025296 A2 | 3/1981 | | GB | 2145112 | 2/1985 |
| EP | 0 046 345 A2 | 2/1982 | | GB | 2 144 542 A | 3/1985 |
| EP | 0 068 404 B1 | 1/1983 | | GB | 2 153 521 A | 8/1985 |
| EP | 0 026 770 B1 | 3/1983 | | GB | 2 243 681 A | 11/1991 |
| EP | 0 029 662 B1 | 2/1984 | | GB | 2 360 360 A | 9/2001 |
| EP | 0 025 296 B1 | 5/1985 | | JP | 61139747 (A) | 6/1986 |
| EP | 0140616 | 5/1985 | | JP | 61159135 (A) | 7/1986 |
| EP | 0 158 147 A2 | 10/1985 | | JP | 2024535 | 1/1990 |
| EP | 0 160 201 A2 | 11/1985 | | JP | 4126064 (A) | 4/1992 |
| EP | 0 229 814 B1 | 7/1987 | | JP | 4126065 (A) | 4/1992 |
| EP | 0 246 604 A2 | 11/1987 | | JP | 4126066 (A) | 4/1992 |
| EP | 0288029 B1 | 4/1988 | | JP | 4126079 (A) | 4/1992 |
| EP | 0276166 A2 | 7/1988 | | JP | 4126080 (A) | 4/1992 |
| EP | 0 289 677 A2 | 11/1988 | | JP | 4126081 (A) | 4/1992 |
| EP | 0 316 173 A1 | 5/1989 | | WO | WO 84/01265 A1 | 4/1984 |

| | | |
|---|---|---|
| WO | WO 85/04014 A1 | 9/1985 |
| WO | WO 88/07198 | 9/1988 |
| WO | WO 89/04470 A1 | 5/1989 |
| WO | WO 89/04471 A1 | 5/1989 |
| WO | WO 90/13315 A1 | 11/1990 |
| WO | WO 9105236 | 4/1991 |
| WO | WO 92/08120 A1 | 5/1992 |
| WO | WO 92/17288 A1 | 10/1992 |
| WO | WO 93/10803 | 6/1993 |
| WO | WO 9317322 A1 | 9/1993 |
| WO | WO 94/22001 A1 | 9/1994 |
| WO | WO 96/04542 A1 | 2/1996 |
| WO | WO 96/12171 A2 | 4/1996 |
| WO | WO 96/12172 | 4/1996 |
| WO | WO 96/12173 A1 | 4/1996 |
| WO | WO 96/31764 | 10/1996 |
| WO | WO 96/33806 A1 | 10/1996 |
| WO | WO 97/29354 A1 | 8/1997 |
| WO | WO 97/30338 A1 | 8/1997 |
| WO | WO 97/35189 A1 | 9/1997 |
| WO | WO 97/43620 A1 | 11/1997 |
| WO | WO 89/04472 A1 | 5/1998 |
| WO | WO 98/34094 A1 | 8/1998 |
| WO | WO 98/48259 | 10/1998 |
| WO | WO 98/57152 A1 | 12/1998 |
| WO | WO 99/05504 A2 | 2/1999 |
| WO | WO 99/33956 A1 | 7/1999 |
| WO | WO 99/38883 A1 | 8/1999 |
| WO | WO 99/42810 A1 | 8/1999 |
| WO | WO 99/44035 | 9/1999 |
| WO | WO 99/44037 A1 | 9/1999 |
| WO | WO 99/47906 A1 | 9/1999 |
| WO | WO 99/60397 A1 | 11/1999 |
| WO | WO 9957955 | 11/1999 |
| WO | WO 99/61888 A2 | 12/1999 |
| WO | WO 00/06193 A1 | 2/2000 |
| WO | WO 00/12204 | 3/2000 |
| WO | WO 00/36396 | 6/2000 |
| WO | WO 00/49387 | 8/2000 |
| WO | WO 00/54026 | 9/2000 |
| WO | WO 00/56444 | 9/2000 |
| WO | WO 00/70080 | 11/2000 |
| WO | WO 01/02836 A1 | 1/2001 |
| WO | WO 01/28700 A1 | 4/2001 |
| WO | WO 01029538 | 4/2001 |
| WO | WO 01/40765 A2 | 6/2001 |
| WO | WO 01/40765 A3 | 6/2001 |
| WO | WO 01/42757 A2 | 6/2001 |
| WO | WO 01/51612 A1 | 7/2001 |
| WO | WO 01/61313 A2 | 8/2001 |
| WO | WO 01/68110 A | 9/2001 |
| WO | WO 01/68226 A2 | 9/2001 |
| WO | WO 01/71348 A1 | 9/2001 |
| WO | WO 01/75161 A2 | 10/2001 |
| WO | WO 0175176 | 10/2001 |
| WO | WO 01/85913 A | 11/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/01189 A1 | 1/2002 |
| WO | WO 02/04666 A2 | 1/2002 |
| WO | WO 02/19594 A | 3/2002 |
| WO | WO 02/19943 A1 | 3/2002 |
| WO | WO 02/20850 A2 | 3/2002 |
| WO | WO 02/21102 A2 | 3/2002 |
| WO | WO 02/23163 A1 | 3/2002 |
| WO | WO 02/25269 A2 | 3/2002 |
| WO | WO 02/26114 A2 | 4/2002 |
| WO | WO 02/28311 A1 | 4/2002 |
| WO | WO 02/29106 A2 | 4/2002 |
| WO | WO 02/41906 A2 * | 5/2002 |
| WO | WO 02041906 A2 | 5/2002 |
| WO | 0243574 A2 | 6/2002 |
| WO | WO 02/43486 A1 | 6/2002 |
| WO | WO 02/43574 A3 | 6/2002 |
| WO | WO 02/44319 A2 | 6/2002 |
| WO | WO 02/052244 A2 | 7/2002 |
| WO | WO 02/054044 A2 | 7/2002 |
| WO | WO 02/057775 A1 | 7/2002 |
| WO | WO 02/060880 A1 | 8/2002 |
| WO | 02077011 A3 | 10/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | WO 03020877 A2 | 3/2003 |
| WO | WO 03/056330 A2 | 7/2003 |
| WO | WO 03/056335 A2 | 7/2003 |
| WO | WO 03/072765 A1 | 9/2003 |
| WO | WO 03/078065 A1 | 9/2003 |
| WO | WO 03/078972 A1 | 9/2003 |
| WO | WO 04001401 | 12/2003 |
| WO | WO 2004/006916 A1 | 1/2004 |
| WO | WO 2004/09237 | 1/2004 |
| WO | WO 2004/009237 A2 | 1/2004 |
| WO | WO 2004/009237 A3 | 1/2004 |
| WO | WO 2004/012837 A2 | 2/2004 |
| WO | WO 2004/012837 A3 | 2/2004 |
| WO | WO 2004/017041 A2 | 2/2004 |
| WO | WO 2004/017041 A3 | 2/2004 |
| WO | WO 2004/024227 A2 | 3/2004 |
| WO | WO 2004/024227 A3 | 3/2004 |
| WO | WO 2004/046712 A2 | 6/2004 |
| WO | WO 2004/059282 A2 | 7/2004 |
| WO | WO 2004/003697 A2 | 10/2004 |
| WO | WO 2004/087177 | 10/2004 |
| WO | WO 2004/087177 A1 | 10/2004 |
| WO | WO 2004/088283 A2 | 10/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006/015056 A2 | 2/2006 |
| WO | WO 2006012597 A2 | 2/2006 |
| WO | WO 2006/029653 | 3/2006 |
| WO | WO 2006060770 A2 | 8/2006 |
| WO | WO 2007016090 A2 | 2/2007 |

OTHER PUBLICATIONS

Bruemmer et al., Effect of pyruvate on the function of stallion spermatozoa stored for up to 48 hours, Journal of Animal Science, vol. 80, 2002, p. 12-18.*
Abstracts American Dairy science assocation, American Association of animal science, Journal of animal science, vol. 81, Supplement 1, Journal Dairy, science, vo. 86, Supplement 1, Michael et al, 2003 p. 1-3.*
Biewenga et al., The Pharmacology of the Antioxidant Lipoic Acid, General Pharmacology, vol. 29, p. 315-331, 1997.*
Geva et al., Free radicls, antioxidants and human spermatozoa: clinical implications, Human Reproduction, vol. 13, p. 1422-1424, 1998.*
Wang et al., Reactive Oxygen species generation by seminal cells during crypreservation, Urology, vol. 49, p. 921-925, 1997.*
Packer et al., Alpha-lipoic acid as a biological antioxidant, Free radical biology & medicine, vol. 19, p. 227-250, 1995.*
Vervoort et al., The potent antioxidant activity of the vitamin K cycle on Microsomal lipid peroxidation, Biochemical Pharmacology, vol. 54, p. 871-876, 1997.*
Schenk, J.L., et al., "Cryopreservation of Flow-Sorted Bovine Spermatozoa," Theriogenology, 1999, 52, pp. 1375-1391.

International Search Report for PCT/US2005/026269 dated Dec. 2, 2005, 7 pages.
Bencic, D.C., et al. "Carbon Dioxide Reversibly Inhibits Sperm Motility and Fertilizing Ability in Steelhead (*Oncorhynchus mykiss*)," Fish Phys. And Biochem., 2000, vol. 23, pp. 275-281.
Boatman D.E., et al., "Bicarbonate: Carbon-Dioxide Regulation of Sperm Capacitation, Hyperactivated Motility, and Acrosome Reactions," Biol. of Reprod., 1991, vol. 44, pp. 806-813.
International Search Report for PCT/US2005/010481, dated Oct. 10, 2005, 6 pages.
Garcia, M.A., et al., "Development of a Buffer System for Dialysis of Bovine Spermatozoa Before Freezing. III. Effect of Different Inorganic and Organic Salts on Fresh and Frozen-Thawed Semen," Theriogenology, 1989, vol. 31(5), pp. 1039-1048.
Karow, A.M., et al., "Effects of Temperature, Potassium Concentration, and Sugar on Human Spematozoa Motility: A Cell Preservation Model from Reproductive Medicine," Cryobiology, 1992, vol. 29, pp. 250-254.
Invitation to Pay Additional Fees, Results of Partial International Search, PCT/US2005/010599, dated Sep. 7, 2005.
Baumber, J., et al., "The Effect of Reactive Oxygen Species on Equine Sperm Motility, Viability, Acrosomal Integrity, Mitochondrial Membrane Potential, and Membrane Lipid Peroxidation," J of Andrology, 2000, vol. 21(6), pp. 895-902.
Best, T.P., et al., "Nuclear Localization of Pyrrole-Imidazole Polyamide-Flourescein Conjugates in Cell Culture," PNAS, 2003, vol. 100(21), pp. 12063-12068.
Bruemmer, J.E., et al., "Effect of Pyruvate on the Function of Stallion Spermatozoa Stored for up to 48 Hours," J Anim Sci, 2002, vol. 80, pp. 12-18.
Physiology of Reproduction and Artificial Insemination of Cattle, 1978, 2nd Ed., Chap. 16-18, pp. 442-576, Edited by G.W. Salisbury, N. L. VanDemark, J.R. Lodge, published by W.H. Freeman Co., San Francisco, CA.
Graves, C.N., et al., Metabolism of Pyruvate by Epididymal-Like Bovine Spermatozoa, 1964, J Dairy Sci, vol. 47(12), pp. 1407-1411.
International Search Report for PCT/US2005/010598 dated Jun. 27, 2005, 7 pgs.
De Pauw, M.C., et al., "Sperm Binding to Epithelial Oviduct Explants in Bulls with Different Nonreturn Rates Investigated with a New in Vitro Model," 2002, Biol Reprod, V67, pp. 1073-1079.
Sabeur, K., et al., "Effects of Angiotensin II on the Acrosome Reaction in Equine Spermatozoa,"2000, J Reprod Fert, V120, pp. 135-142.
Millipore Specialty Media, IVF Protocol, http:///www.specialtymedia.com/05Resources/Protocols/ivfprotocol.htm.
D'Occhio, M.J., "Sexing of Sperm in Embryos: Use of Sexed Sperm in AI, IVF, ICSI and Graft,"1999, Animal Breeding Use of New Technologies, Kinghorn, van der Werf and Ryan, Eds., Chapter 1, Introfuction and Chapter 19, pp. 247-264.
Garner, D.L., et al., "Viability Assessment of Mammalian Sperm Using SYBR-14 and Propidium Iodide, " 1995, Biology of Reproduction, vol. 53, pp. 276-284.
Guthrie, H.D., et al., "Flow Cytometric Sperm Sorting: Effects of Varying Laser Power on Embryo Development in Swine," 2002, Molecular Reproduction and Development, vol. 61, pp. 87-92.
Moseley, W. M., et al., "Relationship of Growth and Puberty in Beef Heifers Fed Monensin" J. Anim. Sci. vol. 55 No. 2 p. 357-62 (1982).
Mount, D. E. "Fibrous and Non-fibrous Carbohydrate Supplementation to Ruminants Grazing Forage From Small Grain Crops." M.S. Thesis. Abstr. Colorado State University. (2000).
Muller, W. And Gautier, F. "Interactions of Heteroaromatic Compounds with Nucleic Acids." Euro. J Biochem. 54:358. (1975).
Mullis, K. B. And F. A. Faloona, "Specific Synthesis of DNA in Vitro Via a Polymerase-Catalyzed Chain Reaction" Methods in Enzymology vol. 155 p. 335-350 (1978).
Munne, S. "Flow Cytometry Separation of X and Y Spermatozoa Could be Detrimental to Human Embryos", Hum. Reprod. 9(5): 758 (1994).
Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).
Myers, S. E., et al., "Production Systems Comparing Early Weaning to Normal Weaning With or Without Creep Feeding for Beef Steers." J. Anim. Sci. 77:300. (1999).
Nix, J. P., et al., "Serum Testosterone Concentration, Efficiency of Estrus Detection and Libido Expression in Androgenized Beef Cows." Therio. 49: 1195. (1998).
Nowshari, et al., "Superovulation of Goats with Purified pFSH Supplemented with Defined Amounts of pLH", Therio. vol. 43, p. 797-802 (1995).
NRC. "Nutrient Requirements for Beef Cattle." National Academy of Sci. National Research Council, Washington, DC. (1996).
O'Brien, Justine K. et al., "Preliminary Developments of Sperm Sorting Technology in Non-human Primates", Biology of Reproduction 2001 (Suppl. 1) 64:158.
Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.
Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).
Owen, J. B. "The Maiden Female-A Means of Increasing Meat Production." Proc. Symp. On the Use of Once Bred Heifers and Gilts. (1973).
Ozhin F.V. et al. Artificial insemination of farm animals. Moscow, Izdatelstvo Selskokhozyaastvennoi Literatury, 1961, pp. 350-361 and pp. 380-393.
Pace, M. M. And Sullivan, J. J. "Effect of Timing of Insemination, Nos. Of Spermatozoa and Extender Components on Pregnancy Rates in Mares Inseminated with Frozen Stallion Semen." J. Reprod. Fertil. Suppl. 2001, 23:115-121.
Parrish, J. J., et al., "Capacitation of Bovine Sperm by Heparin", Department of Meat and Animal Science, Biology of Reproduction 38, p. 1171-1180 (1988).
Patterson, D. J., et al., "Estrus Synchronization with an Oral Progestogen Prior to Superovulation of Postpartum Beef Cows" Therio. 48, 1025-33 (1997).
Peippo, J., et al., "Sex Diagnosis of Equine Preimplantation Embryos Using the Polymerase Chain Reaction", Therio. vol. 44:619-627 (1995).
Penfold, L.M.et at., "Comparative Motility of X and Y Chromosome-Bearing Bovine Sperm Separated on the Basis of DNA Content", Mol. Reprod. and Develop. 1998, vol. 50, pp. 323-327.
Perry, E. J., "Historical Background" The Artificial Insemination of Farm Animals. 4th ed. E. J. Perry (ed.) New Brunswick, Rutgers University Press, pp. 3-12. (1968).
Petersen, G. A., et al, "Cow and Calf Performance and Economic-Considerations of Early Weaning of Fall-Born Beef Claves", J. Anim. Sci., 64:15, pp. 15-22. (1987).
Petit, M. "Early Calving in Suckling Herds." in: J.C. Taylor (ed.) *The Early Calving of Heifers and its Impact on Beef Production*. p. 157-176. (1975).
Pickett B.W., et al., Recent Developments in Artificial Inseminatin in Horses Livestock Production Science, 1998.
Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).
Pickett, B. W., et al., "Effect of Seminal Extenders on Equine Fertility." J. Anim. Sci. 40:1136-1143. (1975).
Pickett, B. W., et al., "Influence of Seminal Additives and Packaging Systems on Fertility of Bovine Spermatozoa." J. Anim. Sci. Suppl. Ii. 47:12. (1978).
Pickett, B. W., et al., "Management of the Mare for Maximum Reproductive Efficiency." CSU Anim. Repro. Lab. Bull. No. 06. Fort Collins Co. (1989).
Pickett, B. W., et al., "Procedures for Preparation, Collection, Evaluation and Insemination of Stallion Semen." CSU Exp. Sta. Artira. Reprod. Lab. Gen. Series Bull. 935. (1973).
Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Ewuine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Province, C.A., et al., Cooling Rates, Storage, Temperatures and Fertility of Extended Equine Spermatozoa Therio. vol. 23 (6) p. 925-934, Jun. 1985.

Purse!, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. And J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115 118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of in Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. " Effects of Bovine Folicular Fluid on Maturation of Bovine Oocytes" Theriogenology 41: 383-394, 1994.

Romero-Arrendondo, A. "Effects of Follicular Fluid dring in Virto Maturation of Bovine Oocytes on In Vitro Fertilization and Early Embryonic Development"Biology of Reproduction 55, 1012-1016, 1996.

Romita, A. "Some Considerations on the Beef Situation in Italy." in: J.C. Taylor (ed.) *The Early Calving of Heifers and its Impact on Beef Production*. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume On Embryo Recovery in Mares." J. Equine Vet. Sci. 10:298-300 (1990).

Roy, J. H., "Rearing Dairy-Herd Replacements." Journal of the Society of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., *Artificial Insemination of Sheep*, Chippendale, New South Whales. Publicity Press. p. 83-84 (1976).

Schenk, J. L. "Applying Sperm Sexing Technology to the AI Industry", Proceedings of the 18th Technical Conference on Artificial insemination & Reproduction, Sep. 29-30, 2000.

Schenk, J. L, et al., "Imminent Commercialization of Sexed Bovine Sperm", Proceedings, The Range Beef Cow Symposium XVI p. 89-96 (1999) Greeley Colorado.

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination ", 7th International Symposium on Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. Ii) 76:71. (1998) abstr.

Seidel, G. E. Jr. " Cryopreservation of Equine Embryos" Veterinary Cliniics of North America: Equine Practice vol. 12, No. 1, Apr. 1996.

Seidel, G. E. Jr. " Sexing Bovine Sperm" the AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for in Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. 11124-11127, (1999).

Seidel, G. E. Jr., et al, "Insemination of Heifers With Very Low Numbers of Frozen Spermatozoa", CSU, Atlantic Breeders Cooperative, Lancaster, PA, DUO Dairy, Loveland, CO, Jul. (1996).

Seidel, G. E. Jr., et al, "Insemination of Holstein Heifers With Very Low Numbers of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.; Oct. 1988.

Senger, P. L., et al., "Influence of Cornual Insemination on Conception in Dairy Cattle." J Anim. Sci. 66:3010-3016. (1988).

Shabpareh, V. " Methods for Collecting and Maturing Equine Oocytes in Vitro " Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N. W. "The Response of the Ewe to Pregnant Serum Mare Gonadotropin and to Horse Anterior Pituitary Extract." J. Reprod. Fertil. 14:175 - 177. (1967).

Shilova, A. V., et al., "The Use of Human Chorionic Gonadotropin for Ovulation Date Regulation in Mares." VIIIth Int. Congress on Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," the Journal of Histochemistry and Cytochemistry, vol. 25, No. 7, pp. 784-789, 1977, USA.

Smith, G. C., et al, "USDA Maturity Indexes and Palatability of Beef Rib Steaks." J. Of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

Spectra Physics, The Solid State Laser Company, "Vangaurd 4 Watts of UV from a Quasi-CW, All Solid State Laser," http://www.splasers.com/products/isl_products/vangaurd.html three pp., printed Nov. 14, 2002.

Spectra-Physics Products, "Fcbar" http://www.splasers.com/products/oem_products/ov_fcbar.html two pp. printed Nov.14, 2002.

Spectra-Physics, The Solid State Laser Company, Vanguard 2000-HMD 532, www.specraphysics.com, Copyright 2002.

Spectra-Physics, The Solid State Laser Company, Vanguard 350-HMD 355, www.specraphysics.com Copyright 2002.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", (1998) pp. 1, 39-41, 81-89.

Staigmiller, R.B. " Superovulation of Cattle with Equine Pituitary Extract and Porcine FSH" Theriogenology 37: 1091-1099 1992.

Stap J. et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp, 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stove! R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. And Robinson, J. A., "A Difference in Dry Mass Between the Heads of X and Y-Bearing Human Spermatozoa", J Reprod Fertil. 48, p. 9-15 (1976).

Swanson, E. W. "Future Research on Problems of Increasing Meat Production by Early Calving." in: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ; Animal Prod. 1985 40:401-440.

Tervit, H.R., et al., "Successful Culture in Vitro of Sheep and Cattle Ova", Agricultural Research Council, Unit of Reprod. Physio. And Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE—100—XHP"*, www.tbsp.com, 2 pp., Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Sero., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

van Munster, E. B., et al, "Difference in Sperm Head Volume as a Theoretical Basis for Sorting X & Y-Bearing Spermatozoa: Potentials and Limitations", Therio 52, pp. 1281-1293 (1999).

van Munster, E. B., et al, "Difference in Volume of X- and Y-chromosome Bearing Bovine Sperm Heads Matches Difference in DNA Content" Cytometry vol. 35 p. 125-128 (1999).

van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. In Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Development of a Non-surgical Deep Intra Uterine Insemination Technique", Boar Semen Preservation IV, IVth International Conference on Boar Semen Preservation, Maryland, Aug. 8, 1999, pp. 262-263.

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263., Jun. 2004.

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Welch G., et al., Fluidic and Optical Modifications to a FACS IV for Flow Sorting of X- and Y-Chromosome Bearing Sperm Based on DNA. Cytometry 17 (Suppl. 7): 74. (1994).

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wheeler, T. L., et al., "Effect of Marbling Degree on Beef Palatability in Bos-taurus and Bos-indicus cattle." J. Anim. Sci. 72:3145. (1994).

Wickersham, E. W. And L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Woods, G. L. And Ginther, 0. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

*Hamamatsu, "Photomultiplier Tubes," webpage,* http://www.optics.org/hamarnatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23, (1995).

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. and Develop. 2003. vol. 15, pp. 351-359.

Hollinshead F. K. et al. "Production of lambs of predetermined sex after the insemination of ewes with low numbers of frozen-thawed sorted X- or Y- Chromosome-bearing spermatozoa", Reprod. Fertil. and Develop. 2002, vol. 14, pp. 503-508.

Hollinshead F. K. et al. "Sex-Sorting and Re-cryopreservation of Frozen-Thawed Ram Sperm for in Vitro Embryo Production" Theriogenology , vol. 59. (2003) pp. 209.

Dhali et al. Vitrification of Buffalo (Bubalus Bubalis)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for in Vitro fertiliation and AI, Journal of Animal Science,vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X-and Y- chromosome bearing sperm, Cytometry 25:191-199 (1996).

van Munster, E. B. Interferometry in flow to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/Isrll.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow. Theriogenology: Jan. 1998 vol. 29 No. 1 pp. 125-142.

Blecher, S.R., et al. A new approach to immunological sexing of sperm, Theriogenology, 59, pp. 1309-1321, 1999 vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (Bos taurus) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., in vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., in vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low Numbers of flow sorted fresh and frozen/thawed stallion spermatozoa, Equine Vet J. 2002 Mar;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984; 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: Highspeed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation in First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $IN Asia B. Japan; www.agnet.org/library/article/eb384b.html.

Crichton,E. et al., 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H. et al., Relationship Between Level of Milk Production and Multiple Ovulation in Lactating Dairy Cows Journal of Dairy Sci. 88:2783-2793; American Dairy Science.

Managing The Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelph.ca/dairyedu/biosyntheses.html.

Milk Production, Released Jul. 18, 2006, by the National Agricultural Statistics Service (NASS), Agri. Stats. Board, US Dept of Agri.

De Vries, A. Economic Value of Pregnancy in Dairy Cattle Journal of Dairy Sci. 89:3876- 3885/American Dairy Sci. Assoc. 2006.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, UNJR Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, Sep./Oct. 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, The Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and -D-Glucuron idase Activity as Indicators of Sea Bass Semen Quality; Biology of Reproduction 70,1679-1684 (2004).

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reporduction 16, 228-237 (1997).

Fattouh, EI-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, Vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number Of Accessory Sperm, Fertilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Sixe in Swine J. Animal Sci. 1997. 75:2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (Anser anser L.) gander semen Animal Reproduction Science 80 (2004) 163-173.

Foote, R. H. et al. Sperm Nos. Inseminated in Dairy Cattle and Nonreturn Rates Revisited 1997 J Dairy Science 80:3072-3076.

Conley, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Depariment of Animal Production and Animal Behaviour, Mariensee, Germany.

Grossfeld, R., "Experiments to Improve the Quality of Sex-Sorted Fresh and Frozen Porcine Spermatozoa" PhD thesis of the Faculty of Agricultural Sciences, Georg-Aug. University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development fo sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18(2), 283-284.

Schenk, J.L. et al., Insemination of cow elk with sexed frozen semen, 2003 Theriogenology 59, 514.

BD Biosciences Brochure, BD FACSCalibur Flow Cytometer, the Automated, Multicolor Flow Cytometry System, 2006.

Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, P. 13, 2000.

Presicce, G.A., et al., First established pregnancies in mediterranean italian buffaloes (bubalus bubalis) following deposition of sexed spermatozoa near the utero tubal junction, Reproduction in Domestic Animals, vol. 40, No. 1, Feb. 2005, pp. 73-75(3).

Dielemann, S.J., Superovulation in cattle: from understanding the biological mechanisms to genomics of the oocyte; $23^{rd}$ Annual Meeting A.E.T.E.—Alghero; Sep. 2007.

Hasler, J. F., Factors influencing the success of embryo transfer in cattle; $23^{rd}$ World Buiatrics Congress, Quebec, Canada Jul. 2004.

Mapletoft, R. J. et al., Superovulation in perspective, Bioniche Animal Health, Dec. 2002.

Bahr, G.F. et al., Considerations of volume, mass, DNA, and arrangement of mitochondria in the midpiece of bull spermatozoa, Experimental Cell Research 60 (1970) 338-340.

BD LSR IIi Flow Cytometer, BD Biosciences Clontech Discovery labware Immunocytometry systems Pharmingen Jan. 28, 2004.

Bermudez, D.et al., the immediate effect of IR, laser radiation on rat, germ, cells, was studied by cytophotometric quantification, Scisearch 2001.

Sequent Biotechnologies Inc., Welcome to the Sequent Biotechnologies Inc. website., http://www.sequentbiotech.com/ Dec. 6, 2003.

Brooks, D.E., Manipulation of Mammalian Gametes in Vitro, Biennial Report, Waite Agricultural Research Institute 1986-1989.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).

Chaudhry, P., et al., Casein Kinase Ii activity and polyamine-stimulated protein phosphorylation of cytosolic and plasma membrane protiens in bovine sperm, Archives of Biochemistry and Biophyeics vol. 271, No. 1 pp. 98-106, May 15, 1989.

Chen, Y. et al., Effects of sucrose, trehalose, hypotaurine, taurine, and blood serum on survival of frozen bull sperm, Cryobiology 30,423-431 (1993).

Chapter 16 Semen processing, storage, thawing, and handling, http://nongae.gsnu.ac.kr/~cspark/teaching/chap16.html Sep. 23, 2002.

Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).

Cressman, B.E. MD, et al., Effect of sperm dose on pregnancy rate from intrauterine insemination: a retrospective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Certified Semen Services, CSS Minimum requirements for disease control of semen produced for AI, http://www.naab-css.org/about_css/disease_control-2002.html Sep. 22, 2003.

Culling, "Handbook of Histopathological and Histochemical Techniques, "3rd Ed., Butterworths, pp. 192.

De Grooth, B. et al., Simple delay monitor for droplet sorters, Cytometry 12:469-472 (1991).

Delgado,N. et al., Correlation between sperm membrane destabilization by heparin and aniline blue staining as membrane integrity index, Archives of Andrology40:147-152 (1998).

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell—Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antiobiotic Combination", Theriogenology, 1990, vol. 33(6), pp. 1211-1220.

Cho, et al. A microfluidic device for separating motile sperm from nomotile sprem via inter-streamline crossings.

Ericsson, R. et al., Functional differences between sperm bearing the X- or Y-chromosome.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D.et al., Physiology and Management, Rapid determination on sperm cell concentration in bovine semen by flow cytometry, J Dairy Sci. 76: 86-94 (1993).

Fitzgerald, D., Cell sorting: An enriching Experience, The Scientist Jul. 23, 2001.

Foote,R., The history of artificial insemination: Selected notes and notables, American Society of Animal Science (2002).

Foote, R., Functional differences between sperm bearing the X- or Y-chromosome.

Garner, D., Past, Present and future perspectives on sexing sperm, CSAS Symposium SCSA: 67-78.

Johnson, L. et al., Sex preselection in mammals by DNA: A method for flow separation of X and Y Spermatozoa in humans.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 ( 1994).

Pinkel,D.et al.,Flow cytometry of mammalian sperm progress in DNA and morphology measurement, The Journal of Histochemical and Cytochemistry vol.27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Centola, G.et al., Cryopreservation of human semen. Comparison of cryopreservatives, sources of variability, and prediction of post-thaw survival. PMID: 1601749 May-Jun. 1992.

Courtens, J. et al., Numerical simulation for freezing and thawing mammalian spermatozoa. Evaluation of cell injuries at different depths in bags or straws during all steps of the technique.

Eiman, M.et al., Trehalose-enhanced fluidity of the goat sperm membrane and its protection during freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Young, L.et al., Prolonged feeding of low levels of zearalenone to young boars.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 06, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, a.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. And Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D.et al., Spermatozoa and Seminal Plasma, Reproduction in farm animals 7th edition.

Gadella B,et al., Dynamics in the membrane organization of the mammalian sperm cell and functionality in fertilization, Vet Quart. 21:142-146 (1999).

Garner, D.et al., Chromatin stability in sex-sorted sperm, VII International Congress of Andrology.

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y- Chromosome-bearing mammalian sperm by flow cytometry, Lawrence Livermore National Laboratory, Feb. 8, 1984.

Gledhill, B.et al., Identifing X- and Y- chromosome- bearing sperm by DNA content:Retrospective perspectives and prospective opinions'.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., " Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55: 372-378 ( 1992).

Grogan, W. et al., DNA Analysis and sorting of viable mouse testis cells, The Journal of Histochemistry and Cytochemistry, vol. 29 No. 6 pp. 738-746, (1981).

Hacker-Klom, U.B., et al., Effect of doxorubicin and 4'-epi-doxorubicin on mouse spermatogenesis. Mutation Research International Journal on Mutagenesis vol. 159, pp. 39-46. 1986.

Hargrove, T. et al., Special Techniques, Part B Cryopreservation, Chapter 11B.

Hasler, J., Symposium: Reproductive Technology and Genetic improvementJ. Dairy Sci. 75:2857-2879 (1992).

Held, A.et al., Quasi- Cw Solid- state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, a.et al.,Assessment of sperm quality through Fluorometry and sperm chromatin structure assay in relation to field fertility of frozen-thawed semen from Swedish AI bulls, Theriogenology 55: 947-961 (2001).

Janendran, R.et al., Effect of glycerol and cryopreservation on oocyte penetration by human spermatozoa, PMID: 4025843, Jul. 6, 2006.

Johnson, L., A flow cytometric/ sorting method for sexing mammalian sperm validated by DNA analysis and live births, Cytometry, p. 42 of supplement , Sep. 4, 1990.

Johnson, L., Flow sorting of intact X & Y chromosome-bearingmammalian spermatozoa, the Journal of the Society for Analytical Cytology Cytometry, (1988).

Zhang,M. et al., Development of bovine embryos after in vitro fertilzation of oocytes with a flow cytometrically sorted, stained and unsorted sperm from different bulls, Theriogenology 60: 1657-1663 (2003).

Jones,R.et al., Effect of Osmolality and Phosphate, "Tris", "Tes", "Mes", nd "Herpes" Hydrogen ion buffers on the motility of bull spermatozoa stored at 37 or 5° C, Ausi J. Biol. Sci.25:1047-1055 (1972).

Jones,R., Plasma membrane structures and remodelling during sperm maturation in the epididymis, Journal of Reproduction and Fertility (1998).

Gerrits, Roger J. Application of Biotechnology to Animal Production US Dept. of Agriculture, Beltsville Maryland.

Johnson, L., Separation of X and,Y Chromosome-bearing mammalian sperm by DNA content cytometric analysis and sorting, US Department of Agriculture,.

Johnson, M.,The Macromolecular Organization of membranes and its bearing on events leading up to Fertilization, Journal of Reproduction and Fertility (1975).

Johnson, L., Verified Sex Pre-Selection in Farm Animals.

Johnson, L., Prograss towards achieving sex preselection in farm animals, USDA Agricultural Research Service, (1989).

Keeler, K.et al., Flow microfluorometric analysis of living spermatozoa stained with Hoechst 33342, J. Reprod.Fert. 68:205-212 (1983).

Keij, J.et al., High speed Photodamage cell sorting: An evaluation of the Zapper Prototype, Methods in cell Biology vol. 42, (1994).

Kirchhoff, C.et al., The Molecular biology of the sperm surface:Post-Testicular Membrane Remodelling, the Fate of the Male Germ Cell, (1997).

Krueger, C.et al.,Low dose Insemination in synchronized gilts, Theriogenology 52: 13631373 (1999).

Landetie,J.,lnduction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B.et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J.et al., Orientation measurments of microsphere doublets and metaphase chromosomes in flow, Cytometry 7:575-581 (1986).

Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).

Masaki, J.et al., Effect of bull seminal plasma on the membrane characteristics of boarepididymal spermatozoa.

Maxwell, W.et al.,Physiology of spermatozoa at high dilution rates:The influence of seminal plasma, Theriogenology 52: 1353-1362 (1999).

Mazur, P., The role of Intracellular freezing in the death of cells cooled at supraoptimal rates, Cryobiology 14:251-272 (1977).

McSweeney,K.et al., Abstract: Insemination of lactating holstein cows with sexed frozen/thawed sperm, http://www.cvmbs.colostate.edu/physio/abstract/ges12.html Mar. 16, 2004.

Medeiros,C. et al., Current status of sperm cryopreservation: Why isn't it better? Theriogenology 57: 327-344 (2002).

Meistrich, M., Potential and limitations of physical methods for separation of sperm bearing an X- or Y- chromosome.

Meistrich, M.et al., "Cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al.,"Sexing of Sperm by Flow Cytometry", The Veterinary Record, 1988, pp. 322-324.

Morrier, A.et al., Glycerol addition and conservation of fresh and crypreserved ram spermatozoa, Canadian Journal of AnimalScience, Sep. 2002http://pubs.nrc-cnrc.gc.ca/aicjournals/2002ab/cjas02/sep02/cjas01-045.html.

Moruzzi, J., Selecting a mammalian species for the separationof X- and Y- chromosome-bearing spermatozoa, J. Reprod. Fert. 57:319-323 (1979).

Murthi S. et al., Improved data acquisition system for digital flow cytometry, (2002).

Studt, T., Mems-based Cell Sorter Speeds Clinical Studies, R&D Magazine, Dec.2003: pp. 36-37 as currently presented on and printed from http;//www.rdmag.com 2 pgs.

Gwo-Bin, L.et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983,pp. 11-19,4,Allan R. Liss, Inc.

OcanaQuero, J.et al., Biological effects of helium-neon irradiation on acrosome reaction in bull, Scisearch Journal of Photochemistry and Photobiology, vol. 40 No. 3, pp. 294-298 (1997).

Pangawkar, G. et al., Physical and biochemical characteristics of semen in relation to fertility of Holstein-Friesian bulls, Indian vet. Med.J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Parks, J. Processing and handling bull semen for artificial insemination—Don't add insult to injury!, Department of Animal Science Cornell University.

Partec, Taking flow cytometry to the next generation, Catalogue 2001-2002.

Perez-Pe, R.et al., Semen plasma proteins prevent cold shock membrane damage to ram spermatozoa, Theriogenology 56 (3) : 425-434, Aug. 1, 2001, PMID: 11516122 http.//www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research an International Journal, vol. 95, No. 3, Sep. 1983.

Piumi, F. et al., Specific cytogenetic labeling of bovine spermatozoa bearing X or Y chromosomes using florescent in situ hybridization (FISH), Genet, Sel. vol. 33: 89-98 (2001).

Polge, C., Low-temperature storage of mammalian spermatozoa, Unit of Reproductive Physiology and Biochemistry, Cambridge.

Edited by Bell-Prince, C. , NFCR Newsletter, http://www.ls.lanl.gov/NFCRnewsletterOc98/oct98.html Jan. 6, 2004.

Rasul, Z.et al., Changes in motion characteristics, plasma membrane integrity, and acrosome morphology during cryopreservation of buffalo spermatozoa, Journal of Andrology, vol. 22 No. 2, Mar. 4, 2001.

Rees, William A., et al,Betaine Can Eliminate the Base Pair Composition Dependence of DNA Melting; Biochemistry 1993, 32, pp. 137-144.

Rens, W.et al.,An X-Y paint set and sperm FISH protocol that can be used for validation of cattle sperm separation procedures, Journals of Reproduction and Fertility, 121: 541-546 (2001).

Reyes-Mereno, C.et al., Characterization of Secretory Proteins from cultured Cauda Epididymal Cells that significantly sustain bovine sperm motility, Molecular Reproduction and Development 63: 500-509 (2002).

Rippel,N. et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R.et al., Semen Quality test and their relationship to fertility, 4th National Association of Animal Breeders, (1972).

Schroter, S.et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online,vol. 7 No. 1 75-81,www.rbmonline.com/Article/847, Apr. 16, 2003.

Seidel, George E. Jr. "What about sexed semen?" Hoard's Dairyman, the National Dairy Farm Magazine, May 10, 2001.

Sexing Technologies, Welcome to sexing Technologies, http://www.sexingtechnologies.com/ Dec. 11, 2003.

Shapiro, Howard M. M.D.,Building Flow Cytometers Chapter 9. Practical Flow Cytometry, second edition, Property of Washington University Medical Library.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J.et al., The Relationship between motility and the FITC-BSA binding Properties of Mouse epididymal spermatozoa, The Journal of Experimental Zoology 227: 323- 327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.

Stewart,R., Georgia Beef Challenge, Livestock Newsletter Jan. 2, 2002.

Takacs, T.et al.,Flow Cytometric determination of the sperm cell number In diluted bull semen samples by DNA staining method, Acta Biochim.Biophys.Hung. vol. 22 No.1, pp. 45-57 (1987).

Thurston,L. et al., Identification of Amplified restriction fragment length polymorphism markers linked to genes controlling boar sperm viability following cryopreservation, Biology of Reproduction 66: 545-554 (2002).

Tone,S.,et al., A method of vital staining of mouse eggs using Hoechst dye, Department of Developmential Biology (1986).

Tubman,L.et al., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 Num.7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/april96/april1965.html Mar. 16, 2004.

Welch, G. et al., Sex preselection: Laboratory Validation of the sperm sex ratio of Flow sorted X- and Y- sperm by sort reanal ysis for DNA, Theriogenology 52:1343-1352 (1999).

Welch, G. et al., Fluidic and optical modification to a facs IV for flow sorting of X&Y Chromosomes bearing sperm based on DNA, International Society for Analytical Cytology (1994).

Wiltshire, M. et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D. et al., Changes in sperm plasma membrane lipid diffusibility after hyperactivation during in vitro capacitation in the mouse, The Journal of Cell Biology, vol. 102: 1372-1377(1986).

Wolf, D. et al., Diffusion and regionalization in membranes of maturing ram spermatozoa, The Journal of Cell Biology, vol. 98:1678-1684 (1984).

XY Files, Issue 1 Jun. 1999.

X Y, Inc., Sex selection Procedure, http://www.xyinc.com/sexselect.html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Abdel-Ghaffar, A. E., et al., "Rabbit Semen Metabolism in Rabbit Production in Hot Climates'" Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R. P., et al. "Prospects for Sexing Mammalian Sperm," Animal Reproduction Laboratory College of Veterinary Medicine and Biomedical Sciences, Colorado State University. (1982).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Amoah, E. A. and Gelaye, S., "Biotechnological Advances in Goat Reproduction", J. Anim. Sci. 75(2): 578-585. (1996).

Anderson, V. K., et al., Intrauterine and tiefzervikale Insemination mit Gefriersperma bein Schat (Intrauterine and Deep Cervical Insemination With Frozen Semen in Sheep). Zuchthygiene 8:113-118. (1973).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Baker, R.D., et al., "Effect of Volume of Semen, Number of Sperm and Drugs on Transport of Sperm in Artificially Inseminated Gilts", J. Anim. Sci. 27:88-93. (1968).

Bakker Schut, Tom C. "A New Principle of Cell Sorting by Using Selective Electroportation in a Modified Flow Cytometry," University of Twente, Mar. 10, 1990.

Barnes, F. L. And Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).

Bedford, S .J. and Hinrichs, K., "The Effect of Insemination Volume on Pregnancy Rates of Pony Mares", Therio. 42:571-578. (1994).

Behrman, S. J., et al., "Freeze Preservation of Human Sperm" American Journal of Obstetrics and Gynecology Vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Berger, G. S. "Intratubal Insemination", Fertil. Steril. 48:328-330, (1987).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., et al., "Sexual Dimorphism in IVF Bovine Embryos Produced by Sperm Sorted by High Speed Flow Cytometry", abstr. Therio. 49(1): 359 (1998).

Beyhan, Z., et al., 1999 Sexual Dimorphism in IVM-IVF Bovine Embryos Produced from X and Y Chromosome-Bearing Spermatozoa Sorted by High Speed Flow Cytometry. Theriogenology. 52: 35-48.

Bigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef—Production III. Culling Strategies and Nontraditional Management-Systems", J. Anim. Sci. 65:963. 1987.

Bracher, V. And Allen, W.R., "Videoendoscopic Examination of the Mare's Uterus: I. Findings in Normal Fertile Mares", Equine Veterinary Journal, vol. 24, p. 274-278. 1992.

Braselton, W. E. and McShan, W. H., "Purification and Properties of Follicle Stimulating and Luteinizing Hormones From Horse Pituitary Glands" Arch. Biochem. Biophys. 139:45-48. 1970.

Braun, J. et al, "Effect of Different Protein Supplements on Motility and Plasma Membrane Integrity of Frozen- Thawed Stallion Spermatozoa", Cryobiology (1995) 32:487-492.

Brethour, J. R. and Jaeger, J. R., "The Single Calf Heifer System", Kansas Agric. Sta. Rep of Progress 570. 1989.

Brinsko, S.P. et al., "Artificial Insemination and Preservation of Semen." Veterinary Clinics of North America:Equine Practice Vol. 8 No.1 Apr. 1992 p. 205-218.

Bristol, F. "Breeding Behavior of a Stallion at Pasture With 20 Mares in Synchronized Oestrus" J. Reprod. Fertil. Suppl. 32:71. 1982.

Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Nos. Of Either Unsexed or Sexed Spermatozoa", Therio. vol. 53, p. 1333-1344. 2000.

Buchanan, B.R. " Pregnancy Rates in Mares Following a Single Insemination with a Low Number of Spermatozoa into the Tip of the Uterine Horn" Theriogenology p. 395 1999.

Burns, P. D. and Spitzer, J.C., "Influence of Biostimulation on Reproduction in Postpartum Beef-Cows", J. Anim. Sci. 70:358. 1992.

Burwash, L. D., et al., "Relationship of Duration of Estrus to Pregnancy Rate in Normally Cycling, Non Lactating Mares" J.A.V.M.A. 165:714-716. 1974.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Catt, et al., "Assessment of Ram and Boar Spermatozoa During Cell-Sorting by Flow Cytometry", Reproduction Dom Animal, vol. 32, pp. 251-258. 1997.

Catt, S. L., et al., "Birth of a Male Lamb Derived from an in Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

Celestron: Telescope Basics: www.celestron.com/tb-2ref/htm; 4 pp., Oct. 20, 2003.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. " Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. And Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and in Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonoqraphy* 1st ed. Rantanen, N. W. and McKinnon A.O. (eds.) Williams and Williams, 1998, p. 165-69.

da Silva, Coutinho M.A.." Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

DakoCvtomation, "MoFlo® Sorters"http://www.dakocvtomation.us/prod productrelatedinformation?url=qprod moflo index.htm one page, printed Jun. 26, 2003.

Database up 1 BR9704313 (Alves, De Resende et al) Jun. 4, 1999.

Day, B. N., et al. Birth of Piglets Preselected for Gender Following in Vitro Fertilization of in Vitro Matured Pig Oocytes by X and Y Bearing Spermatozoa Sorted by High Speed Flow Cytometry. Therio. 49(1): 360. 1998 abstr.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the Number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation. "Coat-A-Count"* http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of in Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (Panthera tigris)" J. Reprod. Fertil. 107:53-58. 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analyses of Dna content ofLiving Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertil. Suppl. 35:221-228. 1987.

Evans, M. J. And Irvine, C. H. G. "Induction of Follicular Development, Maturation and Ovulation by Gonadotropin Releasing Hormone Administration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves",Ohio State University Dept. of Animal Scieneces. 1966 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Noveau et tres simple dispositif interferentiel applicable as microscope" Optica Acta 9, p. 395-408. 1962.

Fugger, E. F. "Clinical Experience with Flow Cytometric Separation of Human X- and Y-Chromosome Bearing Sperm", Therio. vol. 52, pp. 1435-1440.1999.

Fuller, Robert R. "Characterizing Submicron Vesicles With Wavelenth-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orientation of Cells." J of Histochem. and Cytochem. 25:781-783. 1977.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma LuteinizingHormone (LH) and Progesterone Levels in Heifers on Restricted Energy Intakes." J. Anim. Sci. 37:728. 1973.

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. Abstract Complete article from Reproductive Technology vol. 12 # 1 Apr. 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." in: J.C. Taylor (Ed.) *The Early Calving of Heifers and Its Impact on Beef Production.* 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamamatsu. "Technical Information, Optical Detector Selection: a Delicate Balancing Act", web page, http://www.optics.org/hamamatsu/photodiode.html, printed on 4/15/00, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." in: J.C. Taylor (Ed.) *The Early Calving of Heifers and its Impact on Beef Production.* 123 (1975).

Hawk, H. W., et al., "Fertilization Rates in Superovulating Cows After Deposition of Semen on the Infundibulum Near the Uterotubal Junction or After Insemination with High Number of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," Sci. Am. 1976; 234, pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine." Science, Oct. 1977.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (*Mustela putorious furo*) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 1989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. And Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-66.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." in: J.C. Taylor (Ed.) *The Early Calving of Heifers and its Impact on Beef Production*. 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Flow Cytometric Determination of Spermatozoa Sex Ratio in Semen Purportedly Enriched for X or Y Bearing Spermatozoa", Therio. 1988 29:265 abstr.

Johnson, L.A., "Gender Preselection in Domestic Animals Using Flow Cytometrically Sorted Sperm" J. Anim. Sci. (Supp) I) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: an Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).

Johnson, L.A., "Sex Preselection in Swine: Flow Cytometric Sorting of X- and Y- Chromosome Bearing Sperm to Produce Offspring", Boar Semen Preservation Iv, p. 107-114. (2000).

Johnson, L.A., "Successful Gender Preselection in Farm Animals", Agricultural Biotechnology, p. 439-452. (1998).

Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Modification of a Laser-Based Flow Cytometer for High-Resolution DNA Analysis of Mammalian Spermatozoa" Cytometry 7, pp. 268 - 273 (1986).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. Of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774 -780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. And Fertility, p. 393. (1995).

Kinder, J. E., et al., "Endocrine Regulation of Puberty in Cows and Ewes." J. Repro. And Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. And Boime, I., eds. Serono Symposia, Norwell, MA. p. 19-20.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. And Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lightwave Electronics, "Xcyte," www.LightwaveElecronics.com.

Lindsey, A. C., et al., "Low Dose Insemination of Mares Using Non-Sorted and Sex-Sorted Sperm" Animal Reproduction Science 68 p. 279-89 (2001).

Lindsey, A.C. Hysteroscopic insemination of mares with nonfrozen low-dose unsexed or sex-sorted spermatozoa.

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos in Vitro and in Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. 2001 abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug In Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy," 1996 Biophotonics International.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. Iii. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow ", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized in Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." in: J.C. Taylor (ed.) *The Early Calving of Heifers and its Impact on Beef Production*. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Number of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. And Voss, J. L. Equine Reproduction. Lea and Febiger. Philadelphia, London.

McKinnon, A.O., et al., "Predictable Ovulation in Mares Treated With an Implant of the GnRH Analogue Deslorelin." Eq. Vet. J. 25:321-323. (1993).

McKinnon, a.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25, No. 7, pp. 796-803.

Merton, J., et al., "Effect of Flow Cytometrically Sorted Frozen/Thawed Semen on Success Rate of in Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DNA Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N. A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. And Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 1971 54:548.

Molinia, F. C., et al., "Successful Fertilization After Superovulation and Laparoscopic Intrauterine Insemination of the Brushtail Possum Trichosurus vulpecula, and Tammar Wallaby, Macropus eugenii." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Nos. Of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Parallel European Regional Patent Application No. 05731144.1; Examination report dated Sep. 7, 2007.

Parallel New Zealand Patent Application No. 550198; Examinatin report dated Apr. 2, 2008.

Parallel U.S. Appl. No. 11/092,313, Office action dated Jan. 25, 2008.

Parallel U.S. Appl. No. 11/092,313, Office action dated Oct. 10, 2008.

Parallel U.S. Appl. No. 11/092,313, Office action dated Apr. 29, 2009.

Parallel CN Application No. 200580017376.2, Office action dated Mar. 13, 2009.

Parallel CN Application No. 200580017370.5, Office action dated Mar. 08, 2009.

Parallel CN Application No. 200580017370.5, Office action dated Oct. 17, 2008.

Parallel EP Application No. 05731409.8, Office action dated Jun. 27, 2007.

Parallel EP Application No. 05731409.8, Office action dated Jul. 3, 2009.
Parallel AU Application No. 2005229073, Office action dated Aug. 27, 2009.
Parallel AR Application No. P050101214, Office action dated Nov. 4, 2009.
Parallel AR Application No. P050101214, Office action dated May 5, 2009.
Parallel AU Application No. 2005228893, Office action dated Sep. 16, 2009.
Parallel NZ Application No. 550196, Office action dated Apr. 10, 2008.
Parallel NZ Application No. 550196. Office action dated Oct. 8, 2009.
Bavister, Barry D., A Consistently Successful Procedure for in Vitro Fertilization of Golden Hamster Eggs, Gamete Research, vol. 23, pags. 139-158, 1989.
Chinese Office Action dated Dec. 11, 2009 for Cn parallel application No. 200580017370.5 .
New Zealand Exam Report dated Dec. 11, 2009 for NZ parallel application No. 550196 .
Argentina Exam Report dated Nov. 4, 2009 for AR parallel application P050101214 .
Australian Office Action dated May 20, 2010 in parallel Au application no. 2005229073 .
EP Search Report/ Written Opinion dated Jan. 7, 2010 for parallel EP application No. 09014128.4 .
Parallel Australian Application No. 2005229073. Office Action dated May 20, 2010.
Z. Liu and R.H. Foote, Bull Sperm Motility and Membrane intrgrity in Media Varying in Osmolality, J Dairy Sci vol. 81 p. 1886-1874 (1998).
Parallel U.S. Appl. No. 11/092,313 office action dated Apr. 7, 2010.
Parallel CN Application No. 200580017370.5 office action dated Nov. 13, 2009.
Parallel CN Application No. 200580017370.5 office action dated Apr. 15, 2010.
Parallel NZ Application No. 550196 office action dated 4-21-10.
Parallel Ep Application No. 09014128.4 office action dated Feb. 3, 2010.
Parallel CN Application No. 200580017376.2 office action dated Feb. 24, 2010.
Parallel NZ Application No. 581168 office action dated 11-19-09.
Parallel AU Application No. 2005229073 office action dated May 20, 2010.
Parallel AU Application No. 2005228893 office action dated May 25, 2010.
Parallel Japanese application No. 2007-506489, Office Action dated, Oct. 5, 2010, 5 pages.

* cited by examiner

US 7,892,725 B2

PROCESS FOR STORING A SPERM DISPERSION

REFERENCE TO RELATED APPLICATIONS

This application is a nonprovisional of and claims priority to U.S. Patent Application Ser. No. 60/618,440, filed Oct. 13, 2004, U.S. Patent Application Ser. No. 60/614,178, filed Sep. 29, 2004, and U.S. Patent Application Ser. No. 60/557,407, filed Mar. 29, 2004, the content of each of which is hereby incorporated herein by reference in its entirety.

FIELD OF THE INVENTION

The present invention generally relates to a process of storing sperm cells. More specifically, the present invention relates to the process of storing sorted and unsorted spermatozoa having reduced motility relative to endogenous ejaculated sperm, a process for providing such sperm dispersions for inseminating a female mammal, a process for inseminating a female mammal using such sperm dispersions.

BACKGROUND

The fertilization of animals by artificial insemination (AI) and embryo transplant following in vitro fertilization is an established practice. Because the viability and motility of the sperm used in these procedures affects the outcome of the procedures (i.e., whether the fertilization and insemination procedures successfully result in offspring), it is important that the sperm cells be able to survive the rigors often associated with the insemination process, including for example, the collection, storage, and transportation of the cells.

By way of example, in the livestock production industry, the ability to influence the reproductive outcome toward offspring having one or more preferred characteristics, such as offspring of a particular gender, is often desired. In order to effect such an outcome, semen samples from male mammals are collected, stained with a dye, subsequently sorted into X and Y chromosome-bearing cells, optionally stored for a period of time in a frozen or cooled state, and then transported to the location of breeding, where a female mammal is ultimately inseminated. Each of the steps of this process places a stress on the sperm cells that decreases sperm cell viability or motility, particularly progressive motility.

Salisbury et al. describe a technique for the collection of ejaculated bovine semen directly into a diluent which inhibits cell motility and prevents the absorption of carbohydrates from the surrounding seminal plasma. When the ejaculate is collected into the diluent and the air phase above the liquid is replaced by gassing with 100% $CO_2$, the cells in the ejaculate became immotile. As long as the cells remained in the diluent and air was excluded, the cells remained immotile for several hours at room temperature and for at least 8 days at 5° C.

SUMMARY OF THE INVENTION

Among the various aspects of the present invention is a process for rendering spermatozoa immotile for storage, transport, or fertilization in order to protect the spermatozoa from the rigors of the same. In one embodiment of the invention, therefore, a sperm dispersion, sometimes referred to a sperm suspension, is formed comprising spermatozoa and a composition that down-regulates carbohydrate uptake by the spermatozoa.

Briefly, therefore, the present invention is directed to a process for storing unsorted spermatozoa, the process comprising forming a sperm dispersion, the sperm dispersion comprising spermatozoa, a composition that induces sperm immotility, and an antibiotic, and storing the sperm dispersion.

The present invention is further directed to a process for storing sorted spermatozoa, the process comprising forming a sperm dispersion, the sperm dispersion comprising spermatozoa and a composition that that induces sperm immotility, sorting the sperm dispersion into separate populations, wherein the spermatozoa of one of the populations comprises at least about 65% X chromosome bearing sperm cells or at least about 65% Y chromosome bearing sperm cells, and storing the one population at a temperature of about −4° C. to about 30° C.

The present invention is further directed to a process for inseminating a female mammal, the process comprising inseminating a female mammal with a sperm dispersion, the sperm dispersion comprising immotile spermatozoa and a composition that induces sperm immotility.

The present invention is further directed to a process for providing a fresh sperm dispersion for inseminating a female mammal, the process comprising forming a sperm dispersion, the sperm dispersion comprising spermatozoa and a composition that induces sperm immotility, placing the sperm dispersion in a container for shipment to a remote location, and shipping the sperm dispersion in the container to a remote location within about 24 hours after forming the sperm dispersion.

The present invention is further directed to a combination comprising an elongated container for use in the insemination of a female mammal, and a sperm dispersion, the sperm dispersion comprising immotile spermatozoa and a composition that that induces sperm immotility. The sperm dispersion is contained in the elongated container.

The present invention is further directed to a sperm dispersion comprising immotile spermatozoa, a composition that induces sperm immotility, and a cryopreservative. The sperm dispersion may also contain additives to enhance sperm viability, such as for example, an antibiotic, a growth factor, caproic acid, catalase, or a composition which regulates oxidation/reduction reactions intracellularly and/or extracellularly.

Other aspects and features of the invention will be in part apparent and in part pointed out hereinafter.

DETAILED DESCRIPTION OF THE INVENTION

Surprisingly, it has been determined that spermatozoa having reduced motility, and more particularly a temporarily induced immotility, relative to endogenous ejaculated spermatozoa (of the same species) tend to have a greater capacity for enduring periods of storage and transport without the necessity for freezing the spermatozoa. The spermatozoa may be maintained in a state of reduced motility from about the point at which they are collected from the source mammal until the insemination of a female mammal with the immotile spermatozoa. In a preferred embodiment, therefore, a particular concentration of fresh, unfrozen spermatozoa, either sorted or unsorted, may be prepared for storage, transport, or fertilization which have an increased number of viable cells or an increased number of motile sperm versus the same particular concentration of spermatozoa that have been frozen and subsequently thawed.

As a result of the increased viability of the spermatozoa in sperm dispersions, aliquots of sperm dispersions containing lesser densities of spermatozoa may be used for fertilization or insemination procedures, as a greater percentage of the cells contained in an aliquot of the dispersion (such as for example, the percentage of cells contained in an artificial insemination straw) will be viable, progressively motile, and therefore, potentially capable of fertilizing an egg. Likewise, because a lesser density of sperm cells within an aliquot of a dispersion are required for fertilization or insemination procedures, a single ejaculate, in the form of a sperm dispersion, may be divided into a greater number of aliquots for use in fertilization or insemination procedures.

In accordance with the process of the present invention, a dispersion is formed containing spermatozoa and one or more compositions which inhibit the motility of the spermatozoa; such a state of inhibited motility sometimes being referred to as immotility or sperm quiescence. In general, the dispersions will contain spermatozoa in a density of at least about $1 \times 10^3$ sperm/ml, and more preferably in a density of at least about $0.1 \times 10^6$ sperm/ml of dispersion and generally not in excess of about $5 \times 10^{10}$ sperm/ml and more preferably generally not in excess of about $5 \times 10^8$ sperm/ml of dispersion. For example, in one embodiment the suspensions may contain spermatozoa in a "relatively low" density, i.e., in a density of less than about $1 \times 10^7$ sperm/ml, preferably less than about $1 \times 10^6$ sperm/ml, more preferably about $1 \times 10^3$ to about $5 \times 10^6$ sperm/ml, still more preferably about $1 \times 10^3$ to about $1 \times 10^6$ sperm/ml, even more preferably about $1 \times 10^4$ to about $1 \times 10^5$ sperm/ml, and most preferably about $1 \times 10^5$ sperm/ml of suspension. In an alternative embodiment, the suspensions may contain spermatozoa in an "intermediate" density, i.e., in a density of about $1 \times 10^7$ to about $1 \times 10^8$ sperm/ml of suspension. In yet another alternative embodiment, the suspensions may contain spermatozoa in a "relatively high" density, i.e., in a density of at least about $1 \times 10^8$ sperm/ml, preferably about $1 \times 10^8$ to about $5 \times 10^{10}$ sperm/ml, more preferably about $1.5 \times 10^8$ to about $2 \times 10^{10}$ sperm/ml, even more preferably about $1.5 \times 10^8$ to about $2 \times 10^8$ sperm/ml, and still more preferably about $1.5 \times 10^8$ sperm/ml of suspension. Thus, for example, in one embodiment the dispersion may contain at least about $0.04 \times 10^6$, at least about $1 \times 10^6$, at least about $1.5 \times 10^6$, at least about $2 \times 10^6$, at least about $3 \times 10^6$, at least about $0.5 \times 10^7$, at least about $1 \times 10^7$, at least about $2 \times 10^7$, at least about $3 \times 10^7$, at least about $4 \times 10^7$, at least about $5 \times 10^7$, at least about $6 \times 10^7$, at least about $7 \times 10^7$, at least about $8 \times 10^7$, at least about $9 \times 10^7$, or even at least about $12 \times 10^7$ sperm/ml of dispersion. In an alternative embodiment, the suspension may contain less than about $9 \times 10^5$, less than about $7 \times 10^5$, less than about $5 \times 10^5$, less than about $2 \times 10^5$, less than about $1 \times 10^5$, less than about $1 \times 10^4$, or even less than about $1 \times 10^3$ sperm/ml of suspension.

The density of spermatozoa may vary based upon a number of factors, including, for example, the species of the mammal from which the spermatozoa are obtained. For example, bovine spermatozoa may be in a dispersion at a higher density, but typically in a smaller volume, such as for example $0.5 \times 10^6$ sperm/ml to about $8 \times 10^7$ sperm/ml in a volume of about 0.5 ml to about 25 ml. Swine spermatozoa, however, may be in a dispersion at a lower density, but typically in a greater volume, such as for example $0.04 \times 10^6$ sperm/ml to about $1 \times 10^7$ sperm/ml in a volume of about 50 ml to about 250 ml.

The density of the spermatozoa in sperm dispersions may vary based upon individual mammal or species specific factors. Examples of such factors include, for example, the variations among different species of mammals, variations among the mammals of a single species, and even variations among different ejaculates of a single mammal.

The density of the spermatozoa in the sperm dispersions may also be artificially manipulated to achieve a dispersion of a specific spermatozoa density. Manipulations to the density of spermatozoa in a sperm dispersion, for example, contained in an insemination straw, may be made based upon factors such as the temperature at which the dispersion may be stored, the length of the storage period, whether the spermatozoa in the sperm dispersion are sorted or unsorted, the species of the male mammal from which the spermatozoa were collected, the fertility of the mammal from which the spermatozoa were collected, and the species of the female mammal to be inseminated.

The density of spermatozoa in a sperm dispersion may also be affected by the method in which the sperm cells may be subsequently enriched or sorted. For example, the sperm cells may be sorted using flow cytometry as described in greater detail below. In such an instance, the buffered sperm suspension may typically be of an "intermediate" or "relatively high" density of spermatozoa. Other sorting or enrichment techniques may benefit from a lesser density of spermatozoa, such as a "relatively low" density of spermatozoa, labeled with a marker, such as for example the dyes and labels described herein.

The density of the spermatozoa in a sperm dispersion may also be affected by simply concentrating the spermatozoa, such as for example, by centrifugation. In such an instance, the dispersion would substantially separate into what is commonly referred to as a pellet (a mass of cells containing a minimal amount of fluid) and a supernatant (a soluble liquid fraction). The supernatant may then be decanted without disruption of the pellet, thereby resulting in a relatively dense pellet of sperm cells containing a minimal amount of the inhibitory buffer, the effect being to reduce the volume of the dispersion without changing the components of the dispersion. As a result, the sperm cells of the pellet remain in an immotile state.

In a preferred embodiment, spermatozoa in dispersions of the present invention behave, in certain respects, in a manner characteristic of epididymal spermatozoa; for example, the spermatozoa may be immotile, may have a lesser rate of endogenous respiration, or may have a greater rate of aerobic glycolysis as compared to freshly ejaculated spermatozoa. Advantageously, the inhibited spermatozoa have the ability, upon separation from the inhibitor(s), to behave in a manner characteristic of ejaculated spermatozoa (and not characteristic of epididymal spermatozoa) with respect to motility and, in one embodiment, with respect to motility and respiration.

In one embodiment, for example, the motility inhibitor reduces path velocity, progressive velocity, or both, as measured by HTM-IVOS sperm analysis (Hamilton-Thorne HTM-IVOS computer assisted sperm analysis system Hamilton-Thorne Research, Beverly Mass.) of at least about 50% of the sperm cells in the dispersion relative to the path velocity, progressive velocity, or both of sperm cells in a fresh ejaculate of the same species. Preferably, the motility inhibitor reduces path velocity, progressive velocity, or both, as measured by HTM-IVOS sperm analysis, of at least about 60% of the sperm cells in the dispersion relative to the path velocity, progressive velocity, or both of sperm cells in a fresh ejaculate of the same species. More preferably, the motility inhibitor reduces path velocity, progressive velocity, or both, as measured by HTM-IVOS sperm analysis, of at least about 70% of the sperm cells in the dispersion relative to the path velocity, progressive velocity, or both of sperm cells in a fresh ejaculate of the same species. Still more preferably, the motility inhibitor reduces path velocity, progressive velocity, or both, as measured by HTM-IVOS sperm analysis, of at least about 80% of the sperm cells in the dispersion relative to the path velocity, progressive velocity, or both of sperm cells in a fresh ejaculate of the same species. Even more preferably, the motility inhibitor reduces path velocity, progressive velocity, or both, as measured by HTM-IVOS sperm analysis, of at least about 90% of the sperm cells in the dispersion relative to the path velocity, progressive velocity, or both of sperm cells in a fresh ejaculate of the same species. Even more preferably, the motility inhibitor reduces path velocity, progressive velocity, or both, as measured by HTM-IVOS sperm analysis, of at least about 95% of the sperm cells in the dispersion relative to the path velocity, progressive velocity, or both of sperm cells in a fresh ejaculate of the same species. Most preferably, the motility inhibitor reduces path velocity, progressive velocity, or both, as measured by an HTM-IVOS sperm analysis, of at least about 99% of the sperm cells in the dispersion relative to the path velocity, progressive velocity, or both of sperm cells in a fresh ejaculate of the same species.

In addition to or in lieu of an inhibitory buffer, the temperature of the sperm cells or the immediate environment surrounding the sperm cells (i.e., a sperm dispersion) may solely be reduced to affect the motility of the cells. Such a reduction in temperature will generally increase immotility. Moreover, for example, the reduction of temperature of the sperm cells or the sperm dispersion may permit a reduction in the concentration of inhibitor used to induce immotility. Accordingly, the sperm dispersion may be at a temperature not in excess of 5° C.; preferably between about 0° C. and about 5° C.; more preferably between about 3° C. and about 5° C.; and most preferably about 5° C. Alternatively, the sperm dispersion may be at a temperature within the range of about 4° C. to about 50° C.; preferably from about 7° C. to about 43° C.; more preferably from about 10° C. to about 39° C.; still more preferably from about 15° C. to about 30° C.; even more preferably from about 17° C. to about 25° C.; and most preferably at about 18° C. Preferably, however, the sperm cells are not exposed to temperatures that substantially detrimentally affect the viability of the cells.

The inhibitor may be any of a range of compositions having a depressive effect upon sperm motility. Such compositions include, for example, sodium/potassium ATPase inhibitors, such as, ouabain; compositions comprising potassium ions; and compositions comprising potassium and sodium ions. For example, relatively high concentrations of potassium ions in the dispersion tend to depress sperm motility. In general, therefore, it is preferred that the dispersion contain a source of potassium ions and that the potassium concentration in the dispersion be at least about 0.05 moles/L. More preferably, the potassium concentration is at least about 0.05 moles/L to about 0.5 moles/L. Still more preferably, the potassium concentration is at least about 0.1 moles/L to about 0.3 moles/L. Most preferably, the potassium concentration is at about 0.173 moles/L. Such dispersions will typically, but not necessarily, also contain a source of sodium ions. When sodium is present, the molar ratio of potassium to sodium is generally equal to or greater than 1:1, respectively, but will generally not exceed a molar ratio of 8:1. Preferably, the molar ratio of potassium to sodium is at least about 1.25:1. Still more preferably, the molar ratio of potassium to sodium is at least about 1.5:1. Still more preferably, the molar ratio of potassium to sodium is at least about 1.75:1. Still more preferably, the molar ratio of potassium to sodium is at least about 1.78:1. In one particular embodiment, the molar ratio of potassium to sodium is at least about 2:1. In yet another embodiment, the molar ratio of potassium to sodium is at least about 3:1. In still another embodiment, the molar ratio of potassium to sodium is at least about 4:1. In still another embodiment, the molar ratio of potassium to sodium is at least about 5:1. In still another embodiment, the molar ratio of potassium to sodium is at least about 6:1. In still another embodiment, the molar ratio of potassium to sodium is at least about 7:1. In still another embodiment, the molar ratio of potassium to sodium is at least about 8:1.

The sperm dispersion may additionally comprise an ion or source of carbon dioxide capable of increasing or aiding in the inhibition of sperm motility. This source of carbon dioxide may be in the form of a component of the dispersion, such as, for example, one or more carbonates, or may be in the form an atmosphere of gas above the dispersion having a positive partial pressure of carbon dioxide in excess of the natural partial pressure of carbon dioxide in ambient air. Alternatively, the source of carbon dioxide may be a combination of both a component of the dispersion and an atmosphere of gas above the dispersion having a positive partial pressure of carbon dioxide in excess of the natural partial pressure of carbon dioxide in ambient air.

In one presently preferred embodiment, the sperm dispersion comprises $NaHCO_3$ and $KHCO_3$, thereby providing a source of potassium and sodium ions as well as a partial pressure of carbon dioxide. For example, in one presently preferred embodiment, the dispersion comprises $NaHCO_3$ and $KHCO_3$ in an aqueous solution, preferably $NaHCO_3$, $KHCO_3$, and $C_6H_8O_7.H_2O$ in water. In general, the $KHCO_3$ concentration in the dispersion may be at least about 0.05 moles/L. More preferably, the $KHCO_3$ concentration is at least about 0.05 moles/L to about 0.5 moles/L. Still more preferably, the $KHCO_3$ concentration is at least about 0.1 moles/L to about 0.3 moles/L. Most preferably, the $KHCO_3$ concentration is at about 0.173 moles/L. When $NaHCO_3$ is present, the molar ratio of $KHCO_3$ to $NaHCO_3$ may be as described above with respect to the molar ratio of potassium to sodium.

When $C_6H_8O_7.H_2O$ is present in the dispersion, the molar ratio of $KHCO_3$ to $NaHCO_3$ may be as described above. The molar ratio of $KHCO_3$ to $C_6H_8O_7.H_2O$ may generally be equal to or greater than 1:1, respectively, but will generally not exceed a molar ratio of 8:1. Preferably, the molar ratio of $KHCO_3$ to $C_6H_8O_7.H_2O$ is from at least about 1.25:1. Still more preferably, the molar ratio of $KHCO_3$ to $C_6H_8O_7.H_2O$ is at least about 1.5:1. Still more preferably, the molar ratio of $KHCO_3$ to $C_6H_8O_7.H_2O$ is at least about 1.75:1. In one particular embodiment, the molar ratio of $KHCO_3$ to $C_6H_8O_7.H_2O$ is at least about 1.78:1. In another particular embodiment, the molar ratio of $KHCO_3$ to $C_6H_8O_7.H_2O$ is at least about 2:1. In yet another embodiment, the molar ratio of $KHCO_3$ to $C_6H_8O_7.H_2O$ is at least about 3:1. In still another embodiment, the molar ratio of $KHCO_3$ to $C_6H_8O_7.H_2O$ is at least about 4:1. In still another embodiment, the molar ratio of $KHCO_3$ to $C_6H_8O_7.H_2O$ is at least about 5:1. In still another embodiment, the molar ratio of $KHCO_3$ to $C_6H_8O_7.H_2O$ is at least about 6:1. In still another embodiment, the molar ratio of $KHCO_3$ to $C_6H_8O_7.H_2O$ is at least about 7:1. In still another embodiment, the molar ratio of $KHCO_3$ to $C_6H_8O_7.H_2O$ is at least about 8:1. In one particularly preferred embodiment, the dispersion is formed using an inhibitory buffer comprising 0.097 moles/L of $NaHCO_3$, 0.173 moles/L of $KHCO_3$, 0.090 moles/L $C_6H_8O_7.H_2O$ in water as disclosed in Salisbury & Graves, *J. Reprod. Fertil.*, 6:351-359 (1963). The sperm cells will generally remain quiescent as long as they are exposed to the motility inhibitor(s).

Experimental evidence to date further suggests that the overall health and other vital characteristics of sperm cells may be improved if the cell dispersion is maintained under an atmosphere that reduces or prevents the diffusion of oxygen into the dispersion. This can be achieved by replacing the atmosphere of gas above the sperm dispersion with an atmosphere having an enhanced partial pressure of, for example, carbon dioxide, nitrogen, or other inert gases relative to ambient air. In a preferred embodiment, the atmosphere over the dispersion has a partial pressure of carbon dioxide of at least about 0.0001 atm, but generally less than about 5 atm at atmospheric pressure. In one embodiment, the partial pressure of carbon dioxide is about 0.5 atm to about 2 atm at atmospheric pressure; in another embodiment, the partial pressure of carbon dioxide is about 0.9 atm to about 2 atm at atmospheric pressure; in another embodiment, the partial pressure of carbon dioxide is about 0.95 atm to about 2 atm at atmospheric pressure.

Quiescent or immotile cells may be returned to an active state by separating the cells from the motility inhibitor or exposing them to air. In addition, the initiation of an active state may be further induced by the dilution of the cells in a physiological saline (Salisbury et al., 1963) or a buffer such as TCA buffer or PBS. Typically, at least about 20%, preferably at least about 50%, more preferably at least about 60%, still more preferably at least about 70%, even more preferably at least about 80%, even more preferably at least about 90%, still more preferably at least about 95%, and most preferably at least about 99% of the cells returned to an active state (i.e., reactivated cells) will have a path velocity, progressive velocity, or both, as measured by HTM-IVOS sperm analysis, that is at least about 50%, preferably at least about 60%, more preferably at least about 70%, still more preferably at least about 80%, even more preferably at least about 90%, even more preferably at least about 95%, and most preferably at least about 99% of the path velocity, progressive velocity, or both of the sperm cells prior to being combined with the motility inhibitor (i.e., of sperm cells of a fresh ejaculate).

The present processes may be used to store, to transport, and to fertilize with both sorted and unsorted spermatozoa. If unsorted spermatozoa are to be stored according to the present process, the spermatozoa may be collected directly into a vessel containing the motility inhibitor to form the sperm dispersion. The sperm dispersion may also contain at least one antibiotic. The sperm dispersion may subsequently be stored for a desired period of time.

If sorted spermatozoa are to be stored according to the present process, the spermatozoa may be collected directly into a vessel containing the motility inhibitor to form the sperm dispersion. Once collected, the sperm cells in the dispersion are sorted according to a multi-step process. In general, the cell sorting process comprises a series of discrete steps, i.e., staining of the collected cells, sorting of the cells, collection of the sorted cells, and optionally, cryoextension of the sorted cells. The sorted cells may then be stored for a desired period of time. Advantageously, the motility inhibitor may be included in sperm dispersions formed or employed in one or more of these steps of the cell sorting process.

I. Collection of the Cell Sample

Whether the inventive process is used to store sorted or unsorted sperm, intact viable bovine, porcine, equine, swine, or other mammalian sperm cells, may be collected and contacted with the motility inhibitor. Various methods of collection of viable sperm are known and include, for example, the gloved-hand method, use of an artificial vagina, and electroejaculation. As an example, a bovine semen sample, typically containing about 0.5 to about 10 billion sperm cells per milliliter, may be collected directly from the source mammal, or from more than one source mammal of the same species, into a vessel containing a motility inhibitor to form a sperm dispersion. Alternatively, the semen sample may be collected into an empty vessel and then subsequently contacted with the motility inhibitor within several minutes to hours after collection to form the sperm dispersion.

In addition to a buffer, the sperm dispersion may also contain a range of additives to enhance sperm viability. Exemplary additives include sterols, lipids, and fatty acids, protein sources, antibiotics, growth factors, caproic acid, catalase, Caprogen, (caproic acid, catalase, and 5% egg yolk), and compositions which regulate oxidation/reduction reactions intracellularly and/or extracellularly.

Exemplary protein sources include egg yolk, egg yolk extract, milk (including heat homogenized and skim), milk extract, soy protein, soy protein extract, serum albumin, bovine serum albumin, human serum substitute supplement, seminal proteins, such as, for example, whole seminal plasma or seminal plasma extracts (see, for example, Parks et al., *Sperm Membrane Phospholipid Peroxidation and Fragmentation: Effects on Sperm Function and Role of Seminal Plasma PAF-Acetylhydrolase,* Proceedings of the 16th Technical Conference on Artificial Insemination & reproduction, 1996, the content of which is hereby incorporated herein by reference), and combinations thereof. Albumin, and more particularly bovine serum albumin (BSA), is a preferred protein source. For example, if included, BSA may be present in the sperm dispersion in an amount of less than about 5.0% (w/v), preferably less than about 2% (w/v), more preferably less than about 1% (w/v), and most preferably in an amount of about 0.1% (w/v).

The use of a protein source, such BSA, alone may initiate the process of capacitation in a percentage of the sperm cells in the dispersion. It is preferred that this process take place in the female reproductive tract. Therefore, in order to inhibit the initiation of capacitation during dilution, as well as during the subsequent staining and sorting, an alternative protein source or a protein substitute may be included in the sperm dispersion. The alternative protein source or protein substitute possess the advantageous effects of a typical protein source, such as BSA, in addition to the ability to inhibit the initiation of capacitation in a larger percentage of the cells in the sperm dispersion. Examples of a alternative protein sources includes human serum substitute supplement (SSS) (Irvine Scientific, Santa Ana, Calif.) and cholesterol enhanced BSA, while an example of a protein substitute includes a polyvinyl alcohol, such as for example, a low to medium viscosity polyvinyl alcohol generally of a molecular weight of about 30,000 to about 60,000. Generally, if included, these compositions will be present in the same amounts as disclosed above with respect to BSA, with the total albumin content of the buffer or buffered solution generally not exceeding about 5.0% (w/v).

Exemplary compositions which regulate oxidation/reduction reactions intracellularly and/or extracellularly include for example pyruvate, vitamin K, lipoic acid, glutathione, flavins, quinones, superoxide dismutase (SOD), and SOD mimics. If included in the sperm dispersion, such a composition may be present in a concentration sufficient to effect the protective effect without detrimentally affecting sperm health. Exemplary concentration ranges include from about 10 μM to about 20 mM depending upon such factors as the particular composition being used or the concentration of sperm in the dispersion. For example, pyruvate may be present in the sperm dispersion in a concentration from about 1 mM to about 20 mM, preferably from about 5 mM to about 15 mM, and more preferably about 10 mM. Vitamin K may be present in the sperm dispersion in a concentration from about 1 μM to about 100 μM, preferably from about 10 μM to about 100 μM, and more preferably about 100 μM. Lipoic acid may be present in the sperm dispersion in a concentration from about 0.1 mM to about 1 mM, preferably from about 0.5 mM to about 1 mM, and more preferably about 1 mM.

An antibiotic may be included in the sperm dispersion in order to inhibit bacterial growth. Exemplary antibiotics include, for example, tylosin, gentamicin, lincomycin, spectinomycin, Linco-Spectin® (lincomycin hydrochloride-spectinomycin), penicillin, streptomycin, ticarcillin, polymyxin B, or any combination thereof. If included, the antibiotics may be present in a concentration of about 50 μg to about 800 μg per ml of semen, regardless of whether the semen is neat, buffered, or contains additional substances, such as for example, any of the additives mentioned herein. The Certified Semen Services (CSS) and National Association of Animal Breeders (NAAB) have promulgated guidelines regarding the use of antibiotics with respect to sperm collection and use.

A growth factor may be added to the sperm dispersion in order to help maintain the viability of the sperm cells. Exemplary growth factors include, for example, transforming growth factors ("TGF), such as, for example, TGFβ-1 and TGFβ-2, and insulin-like growth factors ("IGF"), such as for example, IGF-1. Generally, TGF may be present in the sperm dispersion in the form of TGFβ-1 in a concentration of about 0.1 ng/L to about 10 μg/L or as TGFβ-2 in a concentration of about 0.1 ng/L to about 200 ng/L, and IGF may be present in the sperm dispersion in the form of IGF-1 in a concentration of about 0.1 ng/L to about 50 μg/L. The use of such growth factors is well known in the art and is disclosed, for example, in U.S. Patent Application Publication No. 2003/0157473, the content of which is hereby incorporated herein by reference.

Once collected, the cells may be stored in a quiescent state for a desired period of time or alternatively, may be used within several hours. In either event, the cells may be used, for example, in a staining process, a sorting process, or a fertilization process.

A. Sorting of Collected Cells (i) Staining of the Cells

A motility inhibitor may be used to render cells immotile during staining of the cells. A process of staining sperm cells typically comprises the formation of a staining mixture, sometimes referred to as a labeling mixture, containing intact viable sperm cells, a motility inhibitor, and a dye, sometimes referred to as a label. In this aspect of the invention, the motility inhibitor may be contacted with the sperm cells to form a sperm dispersion, and then the dispersion contacted with a DNA selective dye. In this embodiment, the sperm source may be neat semen, or alternatively, a sperm-containing semen derivative obtained by centrifugation or the use of other means to separate semen into fractions.

In an alternative embodiment, the dye may be combined with a motility inhibitor, thereby forming a dye solution. Thus, for example, dye in the form of a neat solid, including a free-flowing powder, or a liquid composition may be combined with the inhibitor to form a dye solution, which may then be combined with neat semen, a sperm dispersion, or a sperm-containing semen derivative.

In any event, the sperm cells will generally remain quiescent as long as they are maintained in the inhibitor. (Salisbury et al., 1963) Preferably, however, the staining mixture is maintained under an atmosphere having an enriched partial pressure of carbon dioxide relative to ambient air; for example, providing an atmosphere over the staining mixture which is 99%+$CO_2$ is generally preferred.

The pH of the staining mixture may be maintained at any of a range of pH's; typically this will be in the range of about 5.0 to about 9.0. For example, the staining mixture may be maintained at a "slightly acid" pH, i.e., from about 5.0 to about 7.0. In this embodiment, the pH is preferably from about 6.0 to about 7.0, more preferably from about 6.0 to about 6.5, and most preferably at about 6.2. Alternatively, the staining mixture may be maintained at a "slightly basic" pH, i.e., from about 7.0 to about 9.0. In this embodiment, the pH is preferably from about 7.0 to about 8.0, more preferably from about 7.0 to about 7.5, and most preferably at about 7.35.

The staining mixture may be formed by using one or more UV or visible light excitable, DNA selective dyes as previously described in U.S. Pat. No. 5,135,759 and WO 02/41906, the content of each of which is hereby incorporated herein by reference. Exemplary UV light excitable, selective dyes include Hoechst 33342 and Hoechst 33258, each of which is commercially available from Sigma-Aldrich (St. Louis, Mo.). Exemplary visible light excitable dyes include SYBR-14, commercially available from Molecular Probes, Inc. (Eugene, Oreg.) and bisbenzimide-BODIPY® conjugate 6-{[3-((2Z)-2-{[1-(difluoroboryl)-3,5-dimethyl-1H-pyrrol-2-yl]methylene}-2H-pyrrol-5-yl)propanoyl]amino}-N-[3-(methyl{3-[({4-[6-(4-methylpiperazin-1-yl)-1H,3'H-2,5'-bibenzimidazol-2'-yl]phenoxy}acetyl)amino]propyl}amino)propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm cells to an unacceptable degree when used in concentrations which enable sorting or enrichment as described elsewhere.

Alternatively, the staining mixture may be formed using fluorescent polyamides, and more specifically polyamides with a fluorescent label or reporter conjugated thereto. Such labels will fluoresce when bound to nucleic acids. Examples of polyamides with a fluorescent label or reporter attached thereto include, for example, those disclosed in Best et al., *Proc. Natl. Acad. Sci. USA*, 100(21): 12063-12068 (2003); Gygi, et al., *Nucleic Acids Res.*, 30(13): 2790-2799 (2002); U.S. Pat. Nos. 5,998,140; 6,143,901; and 6,090,947, the content of each of which is hereby incorporated herein by reference.

Fluorescent nucleotide sequences may also be used to label the sperm cells. Such nucleotide sequences fluoresce when hybridized to a nucleic acid containing a target or complementary sequence, but are otherwise non-fluorescent when in a non-hybridized state. Such oligonucleotides are disclosed, for example, in U.S. Patent Application Publication No. 2003/0113765 (hereby incorporated herein by reference).

Sex specific antibodies may also be used to label the sperm cells in a staining mixture. In this embodiment, for example, a sex specific antibody may be conjugated with a fluorescent moiety (or equivalent reporter molecule). Because the antibody binds to antigens present on only an X chromosome-bearing or, alternatively, a Y chromosome-bearing cell, such cells can be selectively identified based upon their fluorescence (versus the non-fluorescence of an unlabeled cell). Moreover, more than one sex specific antibody, each antibody having a different fluorescent moiety attached thereto, may be used simultaneously. This allows for differentiation of X chromosome-bearing and Y chromosome-bearing cells based upon the differing fluorescence of each.

Luminescent, color-selective nanocrystals may also be used to label sperm cells in a staining mixture. Also referred to as quantum dots, these particles are well known in the art, as demonstrated by U.S. Pat. Nos. 6,322,901 and 6,576,291, each of which is hereby incorporated herein by reference. These nanocrystals have been conjugated to a number of biological materials, including for example, peptides, antibodies, nucleic acids, streptavidin, and polysaccharides, (see, for example, U.S. Pat. Nos. 6,207,392; 6,423,551; 5,990,479, and 6,326,144, each of which is hereby incorporated herein by reference), and have been used to detect biological targets (see, for example, U.S. Pat. Nos. 6,207,392 and 6,247,323, each of which is hereby incorporated herein by reference).

The preferred concentration of the DNA selective or of any other type of dye in the staining mixture is a function of a range of variables which include the permeability of the cells to the selected dye, the temperature of the staining mixture, the amount of time allowed for staining to occur, the concentration of sperm, and the degree of enrichment desired in the subsequent sorting or enrichment step. In general, the dye concentration is preferably sufficient to achieve the desired degree of staining in a reasonably short period of time without substantially detrimentally affecting sperm viability. For example, the concentration of Hoechst 33342, Hoechst 33258, SYBR-14, or BBC in the staining mixture will generally be between about 0.1 µM and about 1.0 M, preferably from about 0.1 µM to about 1000 µM, more preferably from about 100 µM to about 500 µM, still more preferably from about 200 µM to about 500 µM, and even more preferably from about 300 µM to about 450 µM. Accordingly, under one set of staining conditions, the concentration of Hoechst 33342 is preferably about 350 µM. Under another set of staining conditions, the concentration of Hoechst 33342 is about 400 µM. Under still another set of staining conditions the concentration is preferably about 450 µM.

As another example, the concentration of a fluorescent polyamide, such as for example, those described in U.S. Application Publication No. 2001/0002314, will generally be between about 0.1 µM and about 1 mM, preferably from about 1 µM to about 1 mM, more preferably about 5 µM to about 100 µM, even more preferably about 10 µM.

Optionally, the staining mixture may also contain additives to enhance sperm viability. Exemplary additives include an antibiotic or a composition which regulates oxidation/reduction reactions intracellularly and/or extracellularly as discussed above with respect to cell sample collection. These additives may be added to the collection fluid in accordance therewith.

Once formed, the staining mixture may be maintained at any of a range of temperatures; typically, this will be within a range of about 4° C. to about 50° C. For example, the staining mixture may be maintained at a "relatively low" temperature, i.e., a temperature of about 4° C. to about 30° C.; in this embodiment, the temperature is preferably from about 20° C. to about 30° C., more preferably from about 25° C. to about 30° C., and most preferable at about 28° C. Alternatively, the staining mixture may be maintained within an "intermediate" temperature range, i.e., a temperature of about 30° C. to about 39° C.; in this embodiment, the temperature is preferably at about 34° C. to about 39° C., and more preferably about 37° C. In addition, the staining mixture may be maintained within a "relatively high" temperature range, i.e., a temperature of about 40° C. to about 50° C.; in this embodiment, the temperature is preferably from about 41° C. to about 49° C., more preferably from about 41° C. to about 45° C., still more preferably from about 41° C. to about 43° C., and most preferably at about 41° C. Selection of a preferred temperature generally depends upon a range of variables, including for example, the permeability of the cells to the dye(s) being used, the concentration of the dye(s) in the staining mixture, the amount of time the cells will be maintained in the staining mixture, and the degree of enrichment desired in the sorting or enrichment step.

Uptake of dye by the sperm cells in the staining mixture is allowed to continue for a period of time sufficient to obtain the desired degree of DNA staining. That period is typically a period sufficient for the dye to bind to the DNA of the sperm cells such that X and Y chromosome-bearing sperm cells may be sorted or enriched based upon the differing and measurable fluorescence intensity between the two. Generally, this will be no more than about 24 hours; preferably no more than about 10 hours, more preferably, no more than about 2 hours, still more preferably no more than about 90 minutes, even more preferably no more than about 60 minutes, and most preferably from about 5 minutes to about 60 minutes. In a particular embodiment, the period is about 30 minutes.

The length of the staining period and the temperature at which staining occurs are related such that the longer the period of staining, the lower the temperature of staining temperature may be. For example, in one embodiment, the staining may occur at a "relatively low" temperature and for a period of about 3 hours to about 24 hours. Alternatively, the staining may occur at an "intermediate" temperature and for a period of about one-half hour to about 3 hours. In addition, staining may occur at a "relatively high" temperature and for a period of about 10 minutes to about 90 minutes. In a particular embodiment, staining may occur at a temperature of about 4° C. for a period of about 24 hours. In another embodiment, staining may occur at a temperature of about 18° C. for a period of about 4 hours. In yet another embodiment, staining may occur at a temperature of about 41° C. for a period of about 30 minutes.

Accordingly, in one embodiment, a staining mixture is formed comprising sperm cells, a motility inhibitor, and a dye in a concentration from about 100 µM to about 450 µM, and the staining mixture is held for a period of time at a temperature of about 41° C. In another embodiment, the period of time is about 30 minutes. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

In still another embodiment, a staining mixture is formed comprising sperm cells, a motility inhibitor, and a dye in a concentration from about 100 µM to about 450 µM, and the staining mixture is held for a period of time at a temperature of about 28° C. In another embodiment, the period of time is about 3 hours. In another embodiment, the motility inhibitor comprises 0.204 g $NaHCO_3$, 0.433 g $KHCO_3$, and 0.473 g $C_6H_8O_7.H_2O$ per 25 mL of purified water (0.097 moles/L of $NaHCO_3$, 0.173 moles/L of $KHCO_3$, 0.090 moles/L $C_6H_8O_7.H_2O$ in water).

(ii) Sorting or Enriching of the Stained Cells

A motility inhibitor may also be used to render the sperm cells immotile during sorting of the sperm cells. Generally, once the sperm are stained according to the present invention, they may be sorted according to any known means that allows for separation based upon fluorescence. Commonly used and well known methods include flow cytometry systems, as exemplified by and described in U.S. Pat. Nos. 5,135,759, 5,985,216, 6,071,689, 6,149,867, and 6,263,745, International Patent Publications WO 99/33956 and WO 01/37655, and U.S. patent application Ser. No. 10/812,351 (corresponding International Patent Publication WO 2004/088283), the content of each of which is hereby incorporated herein by reference. When sorting according to such methods, the sperm are introduced into the nozzle of a flow cytometer in a sample fluid. In one embodiment, therefore, the sample fluid may comprise the stained sperm cells and a motility inhibitor.

Likewise, the sheath fluid used to surround the stream of sample fluid as it travels through the cytometer may also comprise a motility inhibitor. Generally, the sheath fluid may be introduced into a nozzle of the cytometer using pressurized gas or by a syringe pump. Preferably, the pressurized gas is carbon dioxide or nitrogen, more preferably carbon dioxide. Alternatively, the pressurized gas may be nitrogen.

Optionally, the sample fluid or sheath fluid may also contain additive, such as, an antibiotic, a composition which regulates oxidation/reduction reactions intracellularly or extracellularly, or a growth factor as discussed above with respect to cell sample collection Each of these additives may be added to either fluid in accordance therewith.

Alternatively, the cells of a sperm dispersion may be sorted or enriched using laser steering. This is often referred to as optical trapping or holographic optical trapping. Generally, tightly focused laser light, such as, for example, light focused by a microscope lens, will have a steep intensity gradient. Optical traps use the gradient forces of a beam of light to trap particles based upon the dielectric constant of the beam. To minimize its energy, a particle having a dielectric constant greater than the surrounding medium will move to a region of an optical trap where the electric field is highest. Such devices and methods are described, for example, in WO 2004/012133, U.S. Pat. No. 6,416,190 and related applications and patents, the content of each of which is hereby incorporated herein by reference. Immotility of sperm cells being sorted or enriched according to these methods allows for ease of alignment of cells in the stream and of the laser steering of these cells, thereby enabling a more efficient and accurate sorting or enrichment of the desired cells.

The cells of the sperm dispersion may be sorted accordingly into separate populations, wherein the spermatozoa of the populations comprises a certain percent X chromosome bearing or Y chromosome bearing sperm cells. For example, the spermatozoa of one of the populations may comprise at least about 65% X chromosome bearing or Y chromosome bearing sperm cells, at least about 70% X chromosome bearing or Y chromosome bearing sperm cells, at least about 75% X chromosome bearing or Y chromosome bearing sperm cells, at least about 80% X chromosome bearing or Y chromosome bearing sperm cells, at least about 85% X chromosome bearing or Y chromosome bearing sperm cells, at least about 90% X chromosome bearing or Y chromosome bearing sperm cells, or even at least about 95% X chromosome bearing or Y chromosome bearing sperm cells.

(iii) Collection of the Sorted Cells

Once sorted, the sorted cells are collected in a vessel that contains a collection fluid. Generally, the purpose of the collection fluid includes providing a fluid support for the cells.

In one embodiment, the collection fluid comprises a motility inhibitor. Optionally, the collection fluid may also comprise sterols, lipids, fatty acids, or a protein source. If included in the collection fluid, the sterols, lipids, and fatty acids may be, for example, cholesterol.

If included in the collection fluid, the protein source may be any protein source that does not interfere with the viability of the sperm cells and is compatible with the motility inhibitor. Examples of common protein sources include milk (including heat homogenized and skim), milk extract, egg yolk, egg yolk extract, soy protein and soy protein extract. Such proteins may be used in a concentration from about 1% (v/v) to about 30% (v/v), preferably from about 10% (v/v) to about 20% (v/v), and more preferably about 10% (v/v).

Optionally, the collection fluid may also contain additives such as, an antibiotic or a composition which regulates oxidation/reduction reactions intracellularly or extracellularly as discussed above with respect to cell sample collection. Each of these additives may be added to the collection fluid in accordance therewith.

Accordingly, in a certain embodiment, the collection fluid comprises 0.097 moles/L of $NaHCO_3$, 0.173 moles/L of $KHCO_3$, 0.090 moles/L $C_6H_8O_7 \cdot H_2O$ and 10% (v/v) egg yolk in water, at a pH of about 6.2, more preferably of about 7.0, and even more preferably of about 6.5. Preferably, the collection fluid is maintained under an atmosphere having an enriched partial pressure of carbon dioxide relative to air; for example, the atmosphere may have a partial pressure of carbon dioxide in excess of 0.9, more preferably 0.95 and still more preferably 0.99.

In lieu of the use of a more traditional collection fluid, the sorted cells may be collected into a vessel containing or coated with a cryoextender. Accordingly, in one particular embodiment, the sorted cells are collected into a cryoextender comprising a motility inhibitor. In another embodiment, the sorted cells are collected into a cryoextender comprising a motility inhibitor, water, Triladyle® (Minitube, Verona, Wis., comprising 60 ml glycerol, 24.2 g tris, 13.8 g citric acid, 10.0 g fructose per liter, 5 mg/100 ml tylosin, 25 mg/100 ml gentamycin, 30 mg/100 ml Spectinomycin, and 15 mg/100 ml Lincomycin), egg yolk, and, optionally, pyruvic acid. In yet another embodiment, the collection fluid is the cryoextender comprising 0.097 moles/L of $NaHCO_3$, 0.173 moles/L of $KHCO_3$, 0.090 moles/L $C_6H_8O_7 \cdot H_2O$ in water, and 25 g Triladyl®, 25 g egg yolk, and 10 mM pyruvic acid per 75 mL of water. In still another embodiment, the collection fluid is the cryoextender comprising 0.097 moles/L of $NaHCO_3$, 0.173 moles/L of $KHCO_3$, 0.090 moles/L $C_6H_8O_7 \cdot H_2O$ in water, and 25 g Triladyl®, 25 g egg yolk, per 75 mL of water.

(iv) Cryoextension of the Sorted Cells

Once the sperm have been sorted and collected into collection vessels, they may be used for inseminating female mammals. This can occur almost immediately, requiring little additional treatment of the sperm. In such an instance, the sperm may be stored in their current state for a period of time necessary to, for example, transport the sperm to the location where the insemination is to take place. The sperm may, therefore, be stored and transported in, for example, the collection fluid. Likewise, the sperm may be concentrated to a density appropriate for the particular mammalian species, for example, a density of about of about $50 \times 10^6$ sperm/ml to about $120 \times 10^6$ sperm/ml, in a motility inhibitor and subsequently stored and transported. The selected density depends upon factors such as those discussed below with respect to fertilization, including the species of mammal from which the cells were obtained. Such a range of densities based upon the species of mammal from which the sperm were obtained are well known to those of skill in the art. In any event, the sperm may remain immotile during the storage or transport period, as described in greater detail below.

Likewise, the sperm may also be cooled or frozen for use at a later date. In such instances, the sperm may benefit from the addition of a cryoextender to minimize the impact upon viability or post-thaw motility as a result of cooling or freezing.

A motility inhibitor may be used to render cells in the cryoextender immotile. Generally, a cryoextender may comprise a motility inhibitor, a protein source, and a cryoprotectant. If included, a protein source may be added to provide support to the cells. The protein source may be any protein source that does not interfere with the viability of the sperm cells and is compatible with the motility inhibitor. Examples of common protein sources include milk (including heat homogenized and skim), milk extract, egg yolk, egg yolk extract, soy protein and soy protein extract. Such proteins may be found in a concentration from about 10% (v/v) to about 30% (v/v), preferably from about 10% (v/v) to about 20% (v/v), and more preferably about 20% (v/v).

A cryoprotectant is preferably included in the cryoextender to lessen or prevent cold shock or to maintain fertility of the sperm. Numerous cryoprotectants are known in the art. Selection of a cryoprotectant suitable for use with a given extender may vary, and depends upon the species from which the sperm to be frozen were obtained. Examples of suitable cryoprotectants include, for example, glycerol, dimethyl sulfoxide, ethylene glycol, propylene glycol, trehalose, Triladyl®, and combinations thereof. If included, generally, these cryoprotectants are present in the cryoextender in an amount of about 1% (v/v) to about 15% (v/v), preferably in an amount of about 5% (v/v) to about 10% (v/v), more preferably in an amount of about 7% (v/v), and most preferably in an amount of about 6% (v/v).

In one particular embodiment, the cryoextender comprises a motility inhibitor, water, Triladyl®, egg yolk, and, optionally, pyruvic acid. In yet another embodiment, the cryoextender comprises 0.097 moles/L of $NaHCO_3$, 0.173 moles/L of $KHCO_3$, 0.090 moles/L $C_6H_8O_7.H_2O$ in water, and 25 g Triladyl®, 25 g egg yolk, and 10 mM pyruvic acid per 75 mL of water.

In another particular embodiment, the cryoextender comprises a motility inhibitor, water, Triladyl®, and egg yolk. In yet another embodiment, the cryoextender comprises 0.097 moles/L of $NaHCO_3$, 0.173 moles/L of $KHCO_3$, 0.090 moles/L $C_6H_8O_7.H_2O$ in water, and 25 g Triladyl®, and 25 g egg yolk per 75 mL of water Optionally, the cryoextender may also contain an antibiotic, a growth factor, or a composition which regulates oxidation/reduction reactions intracellularly and/or extracellularly as discussed above with respect to cell sample collection Each of these additives may be added to the cryoextender in accordance therewith.

II. Storage of the Collected Cells

A. Storage Period

Once the cells have been collected from the source mammal, regardless of whether they are optionally sorted thereafter, the cells may be stored for a period of time. The period of storage is dependent upon several factors, including for example, the temperature at which the cells are stored, the number of cells within the storage container, whether the cells are sorted or unsorted, the method of fertilization for which the cells will be used, and the female mammal being fertilized. Generally, for example, the cells may be stored for several hours, such as for example, 2, 4, 8, 12, or 24 hours; for several days, such as for example 1, 2, 3, 4, 5, 6, or 7 days; several weeks, such as for example, 1, 2, 3, or 4 weeks; or several months, such as for example, 1, 2, or 3 months. Typically, cells may be stored for several hours to several days at a temperature of about 5° C. to about 30° C.; for several days to several weeks at a temperature of about −4° C. to about 5° C.; and for several weeks to several months at a temperature of about −196° C. (in liquid nitrogen vapor) to about −4° C.

B. Storage Temperature

The cells may be stored at a range of different temperatures. Selection of a storage temperature is dependent upon several factors, such as for example, the length of time for which the cells will be stored, the concentration of cells within the storage container, whether the cells are sorted or unsorted, the method of fertilization for which the cells will be used, and the female mammal being fertilized. All of these factors affect the number of cells that will remain viable during the storage period. By way of example, generally the greater the length of time for which the cells may be stored, the lower the temperature at which the cells may be stored. The decrease in temperature generally permits a greater percentage of the stored cells to remain viable over a longer period of time.

Accordingly, cells may be stored at a temperature of about −196° C. to about 30° C. For example, cells may be stored at a "relatively low storage temperature," i.e., a temperature range of about −196° C. to about −4° C.; in this embodiment, the temperature is preferably from about −12° C. to about −4° C., more preferably from about −10° C. to about −4° C., and most preferable at about −4° C. Alternatively, the cells may be stored at an "intermediate storage temperature," i.e., a temperature range of about −4° C. to about 5° C.; in this embodiment, the temperature is preferably at about −3° C. to about 5° C., and more preferably about 0° C. to about 5° C., and most preferably at about 5° C. In addition, the cells may be stored at a "moderately high storage temperature," i.e., a temperature range of about 5° C. to about 30° C.; in this embodiment, the temperature is preferably from about 10° C. to about 25° C., more preferably from about 12° C. to about 23° C., and still more preferably from about 15° C. to about 20° C., and most preferably at about 18° C. Advantageously, it has been determined that storage of the cells at 18° C. in the inhibitory buffer provides the added advantage of increased numbers of viable and motile sperm cells, as the rigors of storage at either a higher temperature or at a freezing temperature (i.e., temperature below 0° C.) may be detrimental to sperm viability.

C. Storage Container

The sperm dispersion may be stored in a range of different containers. While the containers may vary in size, generally suitable containers will be capable of containing the sperm dispersion; that is to say, the containers will be constructed of a material that is not susceptible to leaking or deterioration as a result of contact with fluids generally, and sperm dispersions specifically, regardless of whether such contact occurs on the inside or outside of the container. Examples of suitable containers include, for example, flasks, beakers, test tubes, ampules, and other such containers that are generally constructed of glass, plastic, or other similar materials. In a particular embodiment, the container is of a type of construction that is used in the insemination of a female mammal, such as for example, an elongated container. Such elongated containers may generally have a length to diameter ratio of about 1000:1 to about 100:1, preferably a length to diameter ratio of about 900:1 to about 200:1, more preferably a length to diameter ratio of about 800:1 to about 300:1, still more preferably a length to diameter ratio of about 700:1 to about 400:1, even more preferably a length to diameter ratio of about 600:1 to about 400:1, still more preferably a length to diameter ratio of about 500:1 to about 400:1, and in one particular embodiment, a length to diameter ratio of about 450:1. Such elongated containers may generally have a volume of about 0.1 cc to about 100 cc, the volume of the container selected to be used being based upon the species of mammal from which the semen was collected. For example, the volume of such elongated containers may be from about 0.1 cc to about 0.7 cc, preferably a volume of about 0.2 cc to about 0.6 cc, more preferably a volume of about 0.23 cc to about 0.5 cc, and most preferably a volume of about 0.3 cc to about 0.4 cc. In a particular embodiment, the elongated container is what is commonly referred to in the artificial insemination industry as a straw, having a volume of about 0.23 cc and a length to diameter ratio of about 133:1. In another particular embodiment, the elongated container is what is commonly referred to in the artificial insemination industry as a straw, having a volume of about 0.5 cc and a length to diameter ratio of about 67:1. Typically, containers of these volumes are used for the storage of bovine sperm cells.

Alternatively, the volume of the elongated containers may be from about 1 cc to about 100 cc, preferably a volume of about 10 cc to about 75 cc, more preferably a volume of about 15 cc to about 50 cc, still more preferably a volume of about 20 cc, to about 40 cc, and even more preferably a volume of about 25 cc to about 30 cc. In a particular embodiment, the elongated container is what is commonly referred to in the artificial insemination industry as a straw, having a volume of about 25 cc and a length to diameter ratio of about 445:1. Typically, containers of this volume are used for the storage of porcine sperm cells.

The advantage of storing the sperm dispersion in a straw is that the dispersion may remain stored therein until it is to be used for insemination of a female mammal, at which time the contents of the straw may be placed into the uterus of a female mammal. Accordingly, in such an instance, the cells may be maintained in the straw in a motility inhibitor, and therefore, in an immotile state, until the female is inseminated with the dispersion, at which time the in utero fluids will dilute the motility inhibitor, causing the immotile cells to become motile.

III. Fertilization or Insemination

Another aspect of the present invention is the fertilization of an egg or insemination of a female mammal, generally employing the novel process for storing spermatozoa as described above.

Once a sperm dispersion has been formed as discussed in greater detail above with respect to the collection of a sperm cell sample, the sperm dispersion may be used to inseminate a female mammal. Insemination may be performed according to any of a number of methods well known to those of skill in the art. These methods include, for example, artificial insemination, including standard artificial insemination and deep uterine insemination, and other methods well known to those of skill in the art. For example, a sperm dispersion comprising immotile spermatozoa and a composition that induces sperm immotility, may be used to inseminate a female mammal, such as for example, by artificial insemination. In a particular embodiment, the sperm dispersion may be in an elongated container for use in the insemination of a female mammal, and the spermatozoa in the sperm dispersion may remain immotile until the insemination of the female mammal with the dispersion. In another embodiment, the spermatozoa in the sperm suspension are returned to a mobile or active state, such as, for example, by methods described above, and subsequently used to inseminate a female mammal.

Alternatively, the sperm dispersion may be used to fertilize an egg, and more particularly, an egg in vitro, such as for example, by microinjection, including intracytoplasmic sperm injection (ICSI), and other methods well known to those in the art. The fertilized egg may thereafter be introduced into the uterus of a female mammal by any of a number of means well known to those of skill in the art, such as for example embryo transplant.

Insemination of a female mammal or fertilization of an egg in vitro (followed by introduction of the fertilized egg into the uterus of a female) using a sperm dispersion may occur shortly after formation of the sperm dispersion, such as for example, within about 120 hours, preferably within about 96 hours, more preferably within about 72 hours, still more preferably within about 48 hours, and in a particular embodiment, within about 24 hours after formation of the sperm dispersion. In such instances, generally the dispersions may not have been cryopreserved prior to insemination of a female mammal or fertilization of an egg in vitro (i.e., the dispersion is fresh or comprises fresh sperm cells); instead it may have been maintained in a motility inhibitor and/or may have been refrigerated at temperatures of about 4° C. to about 25° C., more preferably from about 10° C. to about 25° C., still more preferably from about 15° C. to about 20° C., and most preferably at about 18° C. Alternatively, the dispersion may be cryopreserved and then thawed prior to insemination of a female mammal or fertilization of an egg in vitro (i.e., the dispersion is frozen/thawed or comprises frozen/thawed sperm cells). Typically, in such an instance, the cryopreserved dispersion will be thawed immediately, such as, for example, within about 15 minutes, before insemination of a female mammal or fertilization of an egg in vitro. Alternatively, the cryopreserved dispersion may be thawed over a period of time or thawed and subsequently stored for a period of time, such as for example less than about 5 days, more preferably less than about 2 days, still more preferably less than about 1 day, and most preferably, less than about 12 hours.

IV. Process for Providing a Fresh Sperm Dispersion

Another aspect of the present invention is providing a fresh sperm dispersion for fertilizing a female mammal generally employing the sperm dispersions described above. Advantageously, the motility inhibitor allows for the collection of spermatozoa from a source mammal into the same, and shipment of the sperm dispersion to the breeding location (i.e., the site at which the female mammal is to be inseminated) without the need to freeze the dispersion. This, therefore, allows for a greater percentage of the sperm in the dispersion to remain viable versus a frozen/thawed dispersion, wherein the rigors of freezing and subsequently thawing the cells in the dispersion increases the risk of detrimentally affecting the viability of the cells. The use of a motility inhibitor in the sperm dispersion, and optionally the storage and/or the transport of the dispersion at a temperature of about 4° C. to about 25° C., preferably at about 10° C. to about 20° C., more preferably at about 15° C. to about 20° C., and most preferably at about 18° C., permits higher fertility rates in female mammals fertilized with the sperm dispersions. The use of a motility inhibitor in the sperm dispersion, and optionally low temperature storage and transport, also permits for the use of a lower sperm concentrations to fertilize female mammals, as a greater number of cells in the dispersion maintain viability.

Once the sperm dispersion is formed as described in greater detail above with respect to sample collection, the dispersion may be placed in a container for shipment to a remote location, such as a farm or other breeding location, which may be, for example, one or more miles (1.69 or more kilometers) away from the location at which the spermatozoa were obtained or the sperm dispersion was formed. The dispersion may be placed in any container that will protect the dispersion from damage as a result of the rigors of shipment. The container may be insulated in order to maintain the dispersion at a suitable temperature, such as for example between about 4° C. to about 25° C., more preferably from about 10° C. to about 25° C., still more preferably from about 15° C. to about 20° C., and most preferably at about 18° C. Moreover, the dispersion may be placed in a container for use in insemination of a female mammal, and then one or more of the insemination containers placed in a container for shipment to the remote location. By way of example, the sperm dispersion may be placed in one or more straws, and the straws then placed in a cooler for shipment to the breeding location.

The container may be shipped by any of the many well known means of shipping items, such as for example, by U.S. mail, by any of a number of overnight shipment services, or by courier service.

Having described the invention in detail, it will be apparent that modifications and variations are possible without departing the scope of the invention defined in the appended claims.

What is claimed is:

1. A process for storing gender enriched spermatozoa, the process comprising the steps of:
   a. forming an immotile sperm dispersion, the immotile sperm dispersion comprising spermatozoa, a composition that induces sperm immotility, and an antibiotic;
   b. sorting the immotile sperm dispersion, while rendered immotile by the composition that induces sperm immotility, into a gender enriched dispersion of X chromosome bearing sperm or Y chromosome bearing sperm; and
   c. storing the gender enriched sperm dispersion.

2. The process of claim 1 wherein the composition that induces sperm immotility comprises potassium and sodium, the molar ratio of potassium and sodium being greater than 1:1, respectively.

3. The process of claim 1 wherein the composition that induces sperm immotility comprises potassium and sodium, the molar ratio of potassium and sodium being greater than 1.75:1.

4. The process of claim 1 wherein the composition that induces sperm immotility comprises potassium and sodium, the molar ration of potassium and sodium being greater than 2:1.

5. The process of claim 1 wherein the composition that induces sperm immotility comprises potassium and sodium, the molar ratio of potassium and sodium being greater than 3:1.

6. The process of claim 1 wherein the sperm dispersion comprises a source of carbonate.

7. The process of claim 1 wherein the immotile sperm dispersion comprises $NaHCO_3$, $KHCO_3$, and $C_6H_8O_7.H_2O$ in water.

8. The process of claim 1 wherein the immotile dispersion comprises a buffer comprising 0.097 moles/L of $NaHCO_3$, 0.173 moles/L of $KHCO_3$, and 0.090 $C_6H_8O_7.H_2O$ in water.

9. The process of claim 1 wherein the immotile sperm dispersion further comprises a DNA selective dye.

10. The process of claim 9 wherein the DNA selective dye is selected from the group consisting of Hoechst 3342, Hoechst 3358, and SYBR-14.

11. The process of claim 1 wherein immotile dispersion is stored in an enlongate container for use in the insemination of a female mammal.

12. The process of claim 11 wherein the elongate container for use in the insemination of a female mammal has a volume from about 0.1 cc to about 100 cc.

13. The process of claim 1 wherein the immotile sperm dispersion further comprises one selected from the group of: vitamin K, Lipoic Acid, and Pyruvate, and combinations thereof.

14. The process of claim 1 wherein prior to the step of storing a cryoextender is added to the gender enriched sperm dispersion.

15. The process of claim 14 wherein the cryoextender further comprises a motility inhibitor.

16. The process of claim 1 wherein the gender enriched sperm dispersion is stored at a temperature between 5° C. and 30° C.

17. The process of claim 1 wherein the gender enriched sperm dispersion is stored at a temperature between −196° C. and 30° C.

18. The process of claim 1 further comprising the step of fertilizing an embryo with the gender enriched sperm dispersion.

19. The process of claim 18 wherein the fertilization occurs within 24 hours of the formation of the gender enriched sperm dispersion.

20. The process of claim 19 wherein the fertilization occurs within 96 hours of the formation of the gender enriched sperm dispersion.

* * * * *